United States Patent
Raidel et al.

(10) Patent No.: US 6,965,058 B1
(45) Date of Patent: Nov. 15, 2005

(54) ABSORBENT ARTICLE

(75) Inventors: Maria Raidel, Nürnberg (DE); Franz Aschenbrenner, Kastl (DE)

(73) Assignee: Hakle-Kimberly Deutschland GmbH, Koblenz (DE)

( * ) Notice: Subject to any disclaimer, the term of this patent is extended or adjusted under 35 U.S.C. 154(b) by 0 days.

(21) Appl. No.: 09/402,059

(22) PCT Filed: Mar. 23, 1998

(86) PCT No.: PCT/EP98/01684

§ 371 (c)(1),
(2), (4) Date: Feb. 14, 2000

(87) PCT Pub. No.: WO98/43684

PCT Pub. Date: Oct. 8, 1998

(30) Foreign Application Priority Data

| Mar. 27, 1997 | (DE) | ................................ 197 13 189 |
| Mar. 27, 1997 | (DE) | ................................ 197 13 190 |
| Feb. 17, 1998 | (DE) | ................................ 198 06 575 |

(51) Int. Cl.[7] ............................................ A61F 13/15
(52) U.S. Cl. ...................................................... 604/367
(58) Field of Search .............................. 604/367–369, 604/374, 375, 378–380, 385.01

(56) References Cited

U.S. PATENT DOCUMENTS

| 3,794,034 A | * | 2/1974 | Jones, Sr. .................... 128/290 |
| 4,988,344 A | * | 1/1991 | Reising et al. .............. 604/368 |
| 5,807,365 A | * | 9/1998 | Luceri ......................... 604/367 |
| 5,904,672 A | * | 5/1999 | LeMahieu et al. .......... 604/378 |
| 5,977,014 A | * | 11/1999 | Plischke et al. ............. 502/401 |

FOREIGN PATENT DOCUMENTS

| DE | 1 907 914 | | 2/1969 | ............ C08G 9/10 |
| EP | 0 339 461 A1 | * | 11/1989 | ........... A61F 13/18 |
| EP | 339 461 | | 11/1989 | ........... A61F 13/18 |

OTHER PUBLICATIONS

Alfred Renner: Kondensationspolymere aus Harnstoff und Formaldehyd mit großer spezifischer Oberfläche, *Die Makromolekulare Chemie*, 1-27, 149, Nr. 3680, 1971.

* cited by examiner

*Primary Examiner*—Larry I. Schwartz
*Assistant Examiner*—C L Anderson
(74) *Attorney, Agent, or Firm*—Pauley Petersen & Erickson

(57) ABSTRACT

Described is an absorbent article comprising a liquid-permeable layer (18) disposed towards the wearer's body when the said article is in use; a liquid-impermeable layer (20) disposed away from the wearer's body when the said article is in use; as well as an absorbent body arranged between the liquid-permeable layer (18) and the liquid-impermeable layer (20). The absorbent body comprises an absorbent material (32) which remains able to flow even after contact with a liquid. In addition, the invention discloses an absorbent article which comprises a liquid-impermeable layer disposed away from the wearer's body when the article is in use, as well as an absorbent body covered by a liquid-permeable layer; with the said absorbent body containing an absorbent material which remains able to flow even after contact with a liquid. In this, the absorbent body is connected to the liquid-impermeable layer in a central area of the said absorbent body.

66 Claims, 15 Drawing Sheets

CROSS-SECTION  W2 < W1

DEFORMATION UNDER PRESSURE FROM ABOVE

T2 < T1

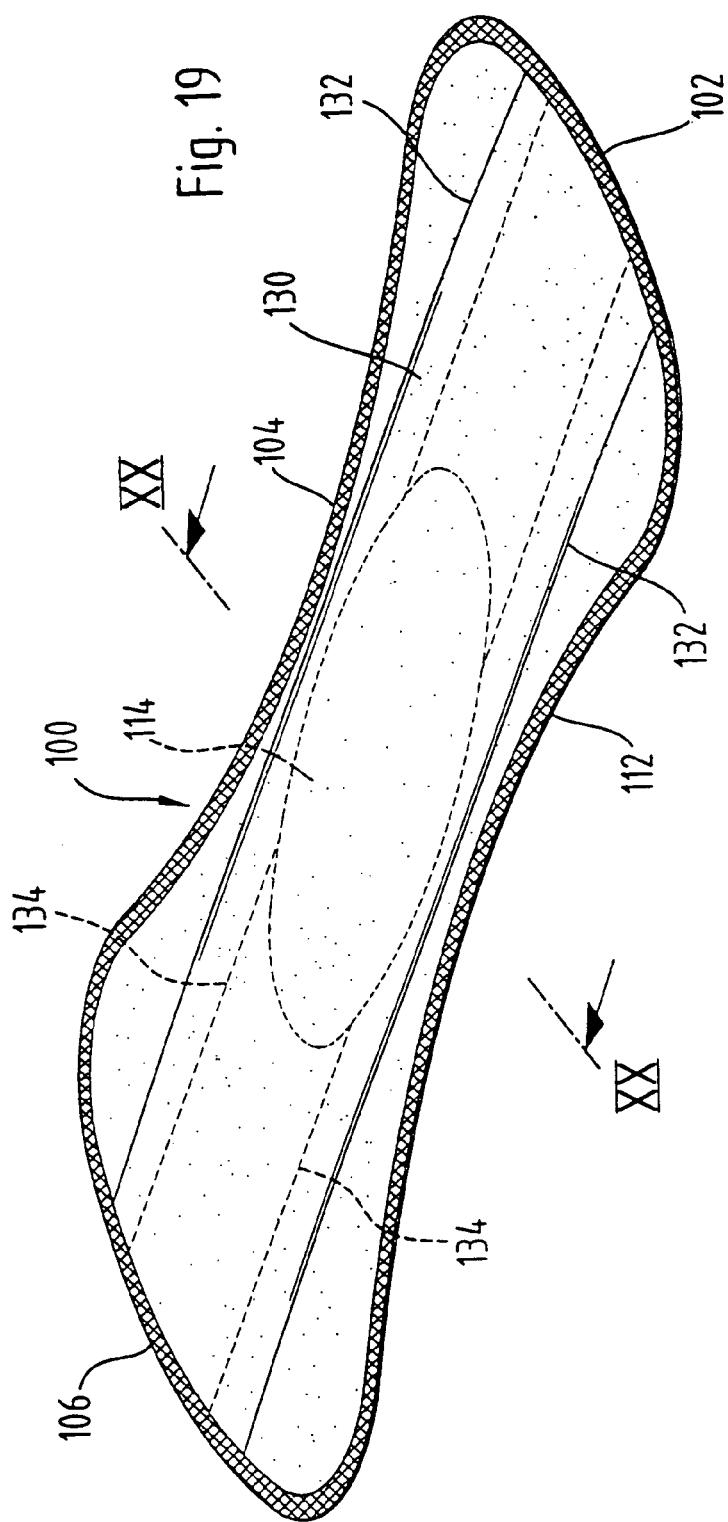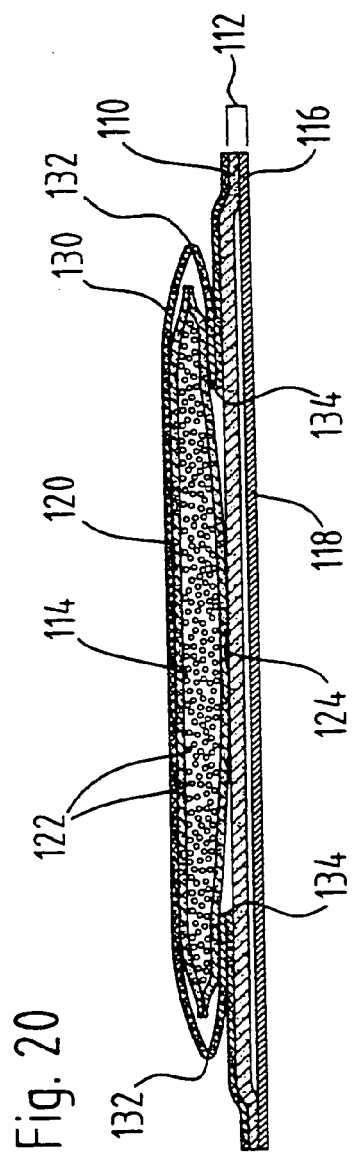

ABSORBENT ARTICLE

FIELD OF THE INVENTION

The present invention relates to absorbent articles.

BACKGROUND OF THE INVENTION

Disposable absorbent articles have been known for many years. They are used for example as sanitary napkins for feminine hygiene, panty liners, children's nappies/diapers or incontinence pads. These disposable absorbent articles share the characteristics that they include a liquid-permeable layer which is disposed towards the wearer's body when the article is in use; a liquid-impermeable layer which is disposed away from the wearer's body when the article is in use; and a liquid-storing layer arranged between these two layers. The liquid-storing layer can for example be made from defiberised cellulose.

The limited liquid-absorption capacity of pure cellulose layers as a liquid-storing material has been a disadvantage with the known disposable absorbent articles. Furthermore, the retention capacity of cellulose, after having been in contact with liquid, is not very pronounced. Finally, deformed cellulose material maintains the shape it has assumed, a fact which is often considered disagreeable by the wearer of the absorbent article. The term 'wearer' as used hereinafter can both be male and female.

In addition, disposable absorbent articles are known whose liquid-storing layer contains superabsorbent materials. Superabsorbent materials are able to absorb many times their dry weight of liquid, which they are able to retain to some degree even under pressure load. Superabsorbent materials are for example known from EP-A-0339461.

One difficulty when using superabsorbent materials in the liquid-storing layer of absorbent articles is that superabsorbent materials experience a volume increase when they are in contact with a liquid, i.e. they swell. This leads to the fact that the absorbent article causes a volume increase and to reduced wearer comfort. Furthermore, the individual components of the superabsorbent materials have a tendency to conglutinate after absorbing a liquid. This leads to a pronounced reduction in the theoretically possible liquid-absorption capacity (so-called gel blocking). Gel blocking results in limited distribution of the liquid which has entered the absorbent article. In the case of contact with a substantial amount of liquid, this might lead to the absorbent article no longer being able to completely absorb the liquid in spite of the theoretical storage capacity still being adequate. This leads to the wearer of the article experiencing a feeling of wetness of the skin and thus discomfort and it also leads to the risk of the wearer's garments becoming soiled. Finally, the absorbent article can also experience permanent deformation as a result of the gel blocking effect, thus further reducing wearer comfort of the article.

SUMMARY OF THE INVENTION

The present invention relates to an absorbent article comprising a liquid-permeable layer disposed towards the wearer's body and a liquid-impermeable layer disposed away from the wearer's body. An absorbent body is arranged between these two layers, the absorbent body absorbing the liquid which has entered the absorbent article through the liquid-permeable layer. The absorbent body of the absorbent article according to the invention is characterized in that it contains an absorbent material which remains able to flow even after having been in contact with a liquid. On the one hand, this novel design results in optimal adaptation of the absorbent article to the wearer's individual body contours, leading to a considerable increase in wearer comfort. On the other hand, the solution according to the invention also results in the article maintaining its functionality even in a deformed condition.

A special embodiment of the absorbent article according to the first aspect is an embodiment in which the liquid-permeable upper cover layer includes folds aligned in longitudinal direction. These folds are configured in such a way that the liquid-permeable layer partly covers the absorbent body also on the side disposed away from the body when the article is worn. On the one hand this is attained by the absorbent body not being connected to the underlying layer along its entire "underside", but only in a small, central area. On the other hand two folds are made into the liquid-permeable layer, which, in longitudinal direction of the absorbent article, also partly encompass the absorbent body on the underside. This embodiment results in the absorbent body remaining flexible in spite of being embedded between the liquid-impermeable backing and the liquid-permeable cover layer, and fitting very well to the anatomical contours of the wearer.

If the liquid-permeable and the liquid-impermeable layers in their marginal areas are interconnected in such a way that a tightly sealed interior space is created, then the absorbent body can be made from a loose, shifting material which remains able to flow even after having been in contact with a liquid, whereby the material can freely move within the entire interior space.

According to a further aspect, the invention concerns an absorbent article with a liquid-impermeable layer which, when the article is used, is disposed away from the body and an absorbent body which is surrounded by a liquid-permeable outer cover, said absorbent body including an absorbent material which remains able to flow even after contact with a liquid, with the absorbent body being connected to the liquid-impermeable layer in a central area of the layer. In this, it is not necessary for the absorbent body and the liquid-impermeable layer to be in direct contact with each other. If on top of the liquid-impermeable layer, one or several other layers are arranged in addition, the absorbent body is attached to the upper side of the uppermost layer.

A further aspect of the invention concerns an absorbent article whose absorbent body is made from an absorbent material, namely polymethylene urea. The absorbent article can comprise a liquid-permeable layer which, when the article is used, is disposed towards the body as well as a liquid-impermeable layer which, when the article is used, is disposed away from the body, with the absorbent body arranged between the liquid-permeable and the liquid-impermeable layer. However, alternative embodiments are also imaginable which, corresponding to the aspect described above, do not include a liquid-permeable upper cover layer but instead merely embed the polymethylene urea material in a liquid-permeable outer cover.

The new concept deviates from known designs in that a part, preferably the main part, of the absorbent components has a grainy consistency, if possible made from spherically-shaped materials. The composition of the material of the absorbent body is such that during wear as well as during contact with a liquid, the absorbent material maintains its ability to flow even after contact with a liquid. Preferably, the absorbent material maintains its ability to flow up to a liquid-absorption of at least 10 ml/g of material. This allows optimal adaptation (ability to follow the wearer's body contours) to the respective body shape of the wearer, during various movements and types of load. In other words, the absorbent body "flows"; during lateral load or lateral pressure by the thighs it can avoid this load or pressure somewhat because material of the absorbent body is shifted or displaced to areas experiencing less load. When the load or the pressure ceases, displaced particles can flow back to the initial position where they are again available for absorbing liquid. On the other hand, as a result of these movements, particles can also be repositioned, and thus absorptive capacity and storage capacity can be used which so far has remained unused. References to "absorbent body" in the present case thus also cover the notion of "storage body".

The absorbent body, which at the same time serves as a storage layer and which contains an absorbent material that remains able to flow even after contact with a liquid, provides the following advantageous characteristics to the absorbent article according to the invention:

Fast liquid-absorption (good penetration into the material able to flow, and good wetting of the material);
Good liquid-retention (locking in the liquid even under pressure load);
Good absorption performance (absorption practically without any increase in volume);
No lumping after contact with liquid;
Best possible adaptation to the wearer's individual body contours;
Article is very soft, combined with high wearer comfort;
Very good liquid-transport and good liquid-distribution;
No collapsing or soaking as happens with cellulose absorbent bodies.

Especially in the case of the absorbent article according to the invention, according to the above-mentioned further aspect, there is optimal adaptation to the anatomical contours of the wearer when the article is worn, because the covered absorbent body is practically "free", i.e. it is not separated from the body of the wearer by a liquid-permeable layer covering the entire article. The liquid emanating from the wearer's body can be absorbed by the absorbent body directly at the place of issue and can then be transferred from there or stored.

Connection between the liquid-impermeable backing and the absorbent body covered by a liquid-permeable layer can take place in any suitable way. For example a connection made by adhesive means has been proven favourable in the mechanical manufacturing of the article according to the invention. However, the backing and absorbent body can for example also be firmly connected to each other by sewing, but of course care must be taken that the liquid-impermeable backing is not damaged in such a way that liquid can penetrate it.

In addition it has been proven advantageous if the absorbent articles according to the invention on the side disposed towards the wearer's body, of the liquid-impermeable layer, comprise a further layer of soft material which serves as secondary storage. This further layer additionally increases the wearer comfort of the absorbent article. In addition, this further layer can also store liquid not yet absorbed by the main absorbent body, whereby of course the absolute storage capacity of the further layer is very much smaller in comparison to the actual absorbent body. Materials suitable for the further layer include coform (polypropylene-cellulose mixtures), airlaid (artificial fibres-cellulose mixtures) and non-woven materials, for example spin-bonded fabrics or card webs.

According to a further aspect of the present invention the absorbent material which remains able to flow even after contact with a liquid can be embedded in a matrix made of fibrous material. In this, the material can be mixed into the fibre matrix in a homogenous way so that the components of the material which remains able to flow even after contact with a liquid are evenly distributed across the fibre structure and are embedded in the said structure. As an alternative to this, the absorbent body can also be of layered construction whereby the absorbent material which remains able to flow even after contact with a liquid is embedded sandwich-like, between two or several layers of fibrous material. Finally, in the last-described sandwich structure in addition, absorbent material can be embedded which absorbent material remains able to flow even after contact with a liquid. Cellulose or a mixture of cellulose and polypropylene, i.e. a so-called coform material, are materials which as fibrous materials are particularly suitable for the above-mentioned purposes. The use of fibrous material leads to a still more optimal distribution of liquid in the absorbent article according to the invention because the fibres have a particular absorbency and can transport liquid in a directional way. The ratio of absorbent material which remains able to flow even after contact with a liquid, to fibrous material, is preferably 1 to 25% by weight to 99 to 75% by weight and in particular 10 to 15% by weight to 90 to 85% by weight.

According to a further aspect of the invention, the absorbent body, apart from the absorbent material which remains able to flow even after contact with a liquid, can also include at least one care substance, adsorptively bound. Primarily this refers to substances which protect the skin of the wearer of the absorbent article according to the invention. For example, extracts of aloe vera, marigold (*calendula*) and/or chamomile (*matricaria*) are suitable substances.

It is particularly advantageous if the care substances are enclosed in microcapsules. In this, the microcapsules can be mixed with the absorbent material which remains able to flow even after contact with a liquid. In this, the outer cover of the microcapsules should be configured in such a way that the microcapsules burst open during wear of the absorbent article according to the invention, thus releasing the substance or the substances. Bursting can for example be caused by pressure, warmth and/or friction. Microencapsulation of substances has for example been known for quite some time in printing technology.

Polymethylene urea of a particular structure is a particularly suitable material for use in the absorbent body or the liquid storage of the absorbent article according to the invention. Even after having been in contact with a liquid, such as in particular urine or menstruation blood, polymethylene urea remains able to flow. The manufacture of polymethylene urea has been known for a long time and can for example take place by acid-catalysed gelling of a urea-formaldehyde solution or of a water-dilutable urea-formaldehyde concentrate, as described for example in Renner, Makromolekulare Chemie 149, 1 (1971) [Macromolecular Chemistry]. In addition, DE-AS-1907914 for example, describes the manufacture of fine-particle amino resin solid materials based on urea-formaldehyde condensates by acid-catalysed polycondensation in aqueous medium.

A desired particle size spectrum can be obtained by suitable process control and/or subsequent granulating. The form of particles, too, can be controlled whereby according to the invention, spherically-shaped particles are particularly suitable. Preferred particle sizes which can be used in the absorbent articles according to the present invention, are smaller than 2 mm; in particular smaller than 0.8 mm. The preferred ranges are 100 to 2000 $\mu$m (0.1 to 2 mm), in particular 200 to 800 $\mu$m (0.2 to 0.8 mm).

When using polymethylene urea polymers as materials which are able to flow in the absorbent articles according to the invention, it is important that during use of the articles no health-endangering substances can arise. In the case of the above-mentioned acid-catalysed polycondensation of formaldehyde and urea in aqueous medium to polymethylene urea, by-products containing ether groups can arise. If one thus tests a commercially available polymethylene urea material for formaldehyde content, then these by-products containing ether groups can be split and can lead to a positive reaction when testing for formaldehyde. The reaction process can be represented by a formula approximately as follows (as per Saechtling, Kunststoff-Taschenbuch [plastics paperback, German language] vol. 26, Carl Hanser Verlag, Munich, Vienna (1995)).

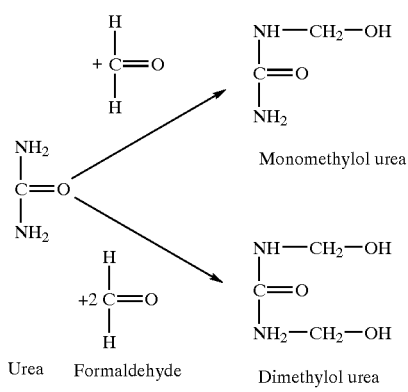

selected reaction conditions (basic, temperature between 50 and 100° C.), dehydration occurs and the reaction products convert to a precondensate. Subsequently by means of acid catalysis, the precondensate is cross-linked to polymethylene urea.

In the above-mentioned processes, apart from polymethylene urea, a smaller quantity of polymethylene urea comprising ether groups results, as shown in the following formula diagram:

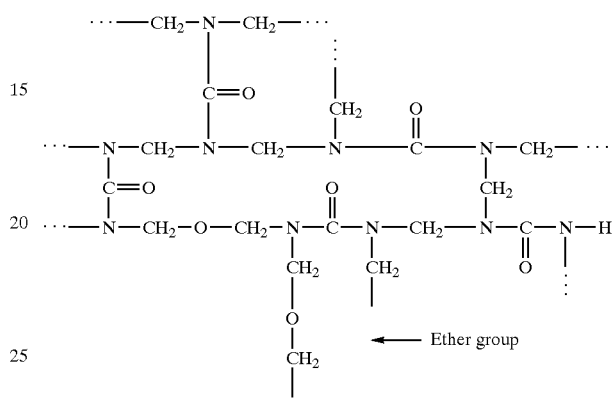

For use in the absorbent articles according to the invention it is advantageous to use material which has few ether bridges as possible, ideally none at all.

It is thus particularly preferred according to the invention, to use a polymethylene urea material free of ether groups in

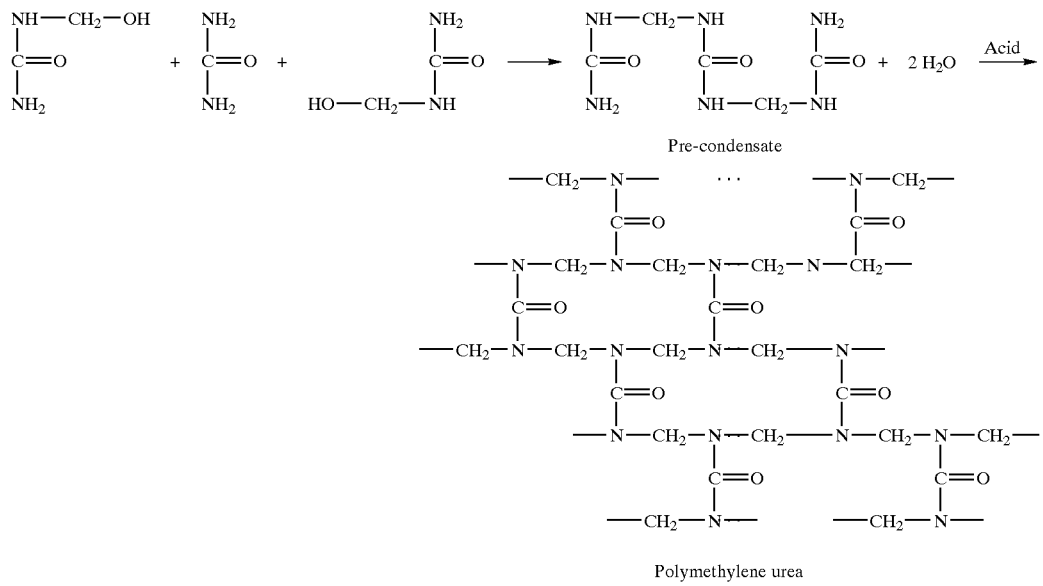

As can be seen from the above formula diagram, during the conversion of urea and formaldehyde, depending on the stoichiometric ratio of the reactants, either monoethylol urea (ratio urea:formaldehyde 1:1) or dimethylol urea (ratio urea:formaldehyde 1:2) results. In the case of ratios between 1:1 and 1:2, both reaction products (mono-methylol urea and dimethylol urea) are formed proportionally. Under the the absorbent article as an absorbent material and storage material which remains able to flow. According to the invention, a traditional synthesis process in which in an addition reaction, urea and formaldehyde are converted to a precondensate and in which subsequently by way of acid-catalysed polycondensation, the polymethylene urea material is produced, is modified to such an extent that after the polycondensation step, the precipitated material is washed with an acid, preferably in the pH range between 1 and 2. Only following the additional acid-wash step can treatment with so-called "formaldehyde catchers" take place. In this way a polymethylene urea material free of ether groups or free of formaldehyde can be obtained.

Polymethylene urea in a particular form can for example be manufactured according to the following process: a 30% formaldehyde solution, urea, as well as if necessary additives, (e.g. protective colloids) are precondensed in a closed vessel while being stirred. The temperature in the mixing vessel is kept between 70 and 90° C.; the pH value between 8 and 9. The production of the precondensate is completed after approximately 30 to 50 minutes. Subsequently, the precondensate is catalytically precipitated with acid, for example with hydrochloric acid, citric acid or sulphaminic acid. In this, the pH value of the acid used is preferably between 1 and 2. The precipitated product is polymethylene urea, which may however still contain ether groups. To remove these ether groups, the polymethylene urea is washed once more with an acid at pH 1 to 2, for example the above-mentioned acids hydrochloric acid, citric acid or sulphaminic acid. Subsequently, the polymethylene urea precipitate is washed with a neutral liquid and then treated with so-called formaldehyde rangers such as sodium sulfite, triethanolamine or a urea-formaldehyde copolymer. Then follows washing and drying of the material obtained, for example at 100 to 110° C. Further after-treatment can follow, for example targeted granulation. Granulation can be supported by using natural substances, such as for example, cellulose, starch or their derivatives.

The granulated polymethylene material obtained in this way is free from ether groups and thus eminently suitable for use in absorbent articles because it is a particularly pure material which does not contain or release any hazardous materials or materials which cause skin irritation.

Apart from polymethylene urea material, the absorbent body of the absorbent article can also contain additional materials. In this, the material composition can be selected in such a way that the above-mentioned functions are taken over by a material or distributed to different materials. Such materials may include: superabsorbers, superabsorbent material in particle shape, super absorbent fibres, zeolites, fibres made of cellulose, cell wool or artificial staple fibres of various length, polystyrene etc.

As regards the characteristics of polymethylene urea particles, it should be added that these particles have a zeolitic structure and are thus similar in effect to zeolites. Zeolites are commonly used in hygiene articles for odour absorption. If polymethylene urea is used as a liquid-absorbent material or liquid-storing material, it is not necessary to use zeolites for odour absorption; this represents a further advantage of the absorbent article according to the invention. Furthermore, polymethylene urea is also advantageous in respect to the quantity of absorbent material to be used. For example when compared with cellulose, the absorption performance of polymethylene urea is more than twice as effective. Also the costs for an absorbent body containing polymethylene urea are considerably lower than the respective costs for a cellulose absorbent body. In comparison to polyacrylates which are used as superabsorbers, the costs for polymethylene urea are in the same order of magnitude as those for cellulose.

Below, the test results of adsorption experiments with polymethylene urea (batch designation P 124), polymethylene urea/polyacrylate mixtures (batch designation P 124+AK) and polyacrylate (batch designation AK) are described. The properties listed in table 1 were determined by means of a tensiometer K121 by Messrs. Krüss.

TABLE 1

| Specimen | δ [degrees] | v rising × $10^2$ [g/s] | Max. water absorption capacity [g/g] |
| --- | --- | --- | --- |
| P124 | 56.8 | 3.266 | 16.1 |
| P124 + 3% AK | 66.1 | 2.42 | 20.3 |
| P124 + 6% AK | 83.1 | 0.715 | 15.5 |
| AK | 76.9 | 1.346 | 1.6 |

The second column of Table 1 shows the respective wetting angle δ of the material investigated. The third column of Table 1 shows the rising velocity in the material, whereby the capillary rise was determined as a weight increase of the material.

As can further be seen from the fourth column of Table 1, 100% P124 has a maximum water absorption capacity of 16.1 g/g material. A mixture of 97% P124 and 3% AK increases the maximum water absorption capacity to 20.3 g/g, and when replacing a further 3% P124 by AK, the value sinks again to 15.5 g/g. All the above-mentioned values show that the respective materials are suitable for use in absorbent bodies of absorbent articles.

The maximum water absorption capacity of the respective materials was determined under conditions where no volume increase for the materials was possible, e.g. any moisture expansion was prevented. This explains the extremely low water absorption capacity of 1.6 g/g of the polyacrylate material.

The polymethylene urea P124 keeps its ability to flow up to a water absorption of 10.5 g/g. Only if the value of 10.5 g/g is exceeded, does the material commence to become slightly lumpy, up to the value of 12.8 g/g. If water absorption exceeds 12.8 g/g, the material structure becomes crumbly and at 18.8 g/g assumes a doughy, viscous consistency. In contrast to this, no ability to flow of pure polyacrylate could be determined, as this material gelled already at the slightest water absorption and led to a sticky bond or adhesion to the wall of the vessel.

Polymethylene urea/polyacrylate mixtures of a ratio 95:5 showed slight moisture expansion of the material and the beginning of gel blocking effects. The higher the percentage of polyacrylate in the mixture, the stronger the moisture expansion and gel blocking observed. Even with high water absorption, no swelling, i.e. no volume increase, was detected with pure polymethylene urea P124. Finally, polymethylene urea and polyacrylate materials at maximum water carrying capacity were subjected to loads. While it was not possible to force water out of polymethylene urea, polyacrylate did give up water when subjected to extended load.

A further aspect of the invention relates to improved prevention of the cause of unpleasant odours during the use of absorbent articles. According to the invention it is proposed to place bactericidal, fungicidal and/or viricidal substances in an adsorptively bound or immobilised way onto or into the absorbent material which remains able to flow even after contact with liquid. If for example polymethylene urea is used as an absorbent material, then it comprises the zeolithic structure described above, i.e. apart from its external surface the material additionally also has a large internal surface which can range from 10 to 700 m²/g. In this it is important that the bactericidal, fungicidal and viricidal substances are immobilised on the absorbent material, because any release of the substances might lead to the wearer of the absorbent article experiencing skin irritation. Above all metabolism products of micro-organisms are responsible for the unpleasant odours in the use of absorbent articles. This means that odour formation can effectively be suppressed or prevented if growth and/or multiplication of the micro-organisms can be inhibited or if these micro-organisms can be killed. The substances mentioned enable inhibition and suppression of the growth of micro-organisms, so that in addition to the already good odour prevention properties of the polymethylene urea material itself, odour formation can be further prevented by the additional use of the above-mentioned bactericidal, fungicidal and viricidal substances. This provides the wearer of an absorbent article according to the invention with further security against undesirable side effects.

For example chlorinated levulinic acid or alkyldimethyl-benzylammoniumhalogenides are suitable bactericidal substances.

Apart from the absorbent article which comprises the components able to flow even after contact with liquid, the absorbent body can comprise additional regions. In such a case the portion of the absorbent body which contains the material able to flow, is preferably configured as at least one core whose length l is smaller than the length L of the absorbent article, and whose width w is smaller than the width W of the absorbent article.

The absorbent body can be connected to the underlying layer along the entire resting surface, for example by an adhesive means. However it might also be adequate if only a part of the absorbent body is connected with the underlying layer. Here again, the most various embodiments are imaginable, for example attachment in strips in that the absorbent body is fixed onto the supporting layer by means of adhesive strips. Generally speaking, the surface or the portion of the surface by which the absorbent body is connected to the underlying layer is smaller than the surface or the surface portion, l×w. The length $\lambda$ of the connection between absorbent body and underlying layer is thus smaller than or equal to the length l, and the width $\beta$ of the connection between absorbent body and underlying layer is smaller than or equal to the width w.

The absorbent body can include one chamber or be divided into several sub-chambers which can be completely separate from each other or can communicate with each other whereby during pressure load on the chamber, particles can then also move to an adjacent chamber.

If the absorbent body and/or the core of the absorbent body is divided into several chambers, then the existing partition walls can be aligned in longitudinal and/or in transverse direction to the absorbent article. For example, division into two sub-chambers can be by a longitudinal or transverse wall. Two longitudinal walls would result in a three-chamber arrangement, and if a transverse wall is added to the two longitudinal walls, then the absorbent body or the core of it is divided into six chambers.

In this, one chamber can be filled to 100% with absorbent polymethylene urea material. It has however been shown to be advantageous if less than the entire chamber containing the material which remains able to flow even after contact with liquid, is filled with material. Thus for example 50 to 100%, preferably 60 to 90%, and in particular 80% of a chamber can be filled with absorbent material. If the absorbent body is of multi-chamber design, then the respective preferred filling quantities apply to individual chambers. If less than 60% of a chamber is filled, then it is additionally advantageous if within individual chambers also so-called flow barriers are provided which prevent accumulation of all absorbent material in one corner of the chamber. Also, as already indicated above, the partition walls between individual chambers can include small apertures so that limited material exchange between individual chambers can take place, i.e. individual chambers can communicate with each other. It is in particular always necessary not to fill individual chambers completely where the chamber includes expandable material, such as for example a superabsorber.

According to a further aspect of the present invention, where there are several chambers forming the absorbent body, these may be filled with various materials.

For example in a design of the absorbent body including three chambers in which the partition walls can be aligned in longitudinal or in transverse direction to the absorbent article, the central chamber can be filled with polymethylene urea or polymethylene urea/superabsorber mixtures, while (in the case of longitudinal partition walls) the laterally situated chambers or (in the case of transverse partition walls) the chambers situated at the front and rear ends can be filled with superabsorbers.

If mixtures for example of polymethylene urea and superabsorbers are used, care must be taken that these mixtures cannot unmix, because this could lead to not all potentially absorbable or storable material being useable, i.e. so-called "dead material" might result.

The present invention thus provides an absorbent article which adapts very well to body contours. The articles are further characterized in that where suitable absorbent materials for the absorbent body are used, they do not experience any volume increase upon contact with a liquid, i.e. they do not expand when moistened. Finally, the articles according to the invention can also optimally absorb liquid in their deformed condition.

Also the absorbent articles according to the invention optimally adapt to the body contours of the wearer. Thus the article can be worn very close to the body (anatomical formfitting) which has the advantage that liquid is absorbed immediately upon exuding from the body, thus preventing the wearer from experiencing any feeling of wetness of the skin. The wearer's feeling of dryness of the skin is also achieved in that with the absorbent articles according to the invention the absorbent material is purposefully centred in the absorbent articles. Finally, the embodiment according to the invention, of the absorbent articles, makes it possible, in the case of a sanitary napkin, for its ends to be kept extremely thin thus allowing very discrete use of a respective article.

Apart from the element, referred to above as an absorbent body, which at the same time serves as a liquid-storage layer (=primary storage), the absorbent article according to the invention can also comprise a further storage layer (so-called secondary storage). This further storage layer is preferably constructed as a web between the absorbent body and the liquid-impermeable layer disposed away from the wearer's body. This material forming the additional storage layer can also be absorbent in order to bring about better liquid-distribution. This additional storage layer is only intended for "emergencies" if the absorbent body (primary storage) for whatever reasons was to exceed its capacity limit. Materials suitable for the additional storage layer (secondary storage), are for example coform materials, cellulose, cellulose-fibre mixtures (air laid), non-woven materials or tissue cotton-wool.

The absorbent articles according to the invention, with the novel absorbent body, can in particular be used in the area of feminine hygiene, for example as a sanitary napkin, in particular an ultra-thin sanitary napkin or a panty liner. Apart from this, the absorbent article according to the invention can however also be designed as a child's disposable nappy/diaper, or an incontinence pad.

If the absorbent article is an article according to the first aspect of the invention, i.e. if it includes a liquid-permeable cover layer which during use of the article is disposed towards the body, then underneath this liquid-permeable layer there can be another cover layer which includes a central aperture (so-called port hole) located above the absorbent body. Respective absorbent articles are for example described in the German patent application No. 19640451. This port hole design is in particular advantageous for feminine hygiene articles.

The absorbent article disclosed in the above-mentioned German patent application can include the following structure. On the side disposed away from the body when the absorbent article is in use, there is a liquid-impermeable layer. Above this liquid-impermeable layer there is a primary storage layer. Above it there is a secondary storage layer. Above the secondary storage layer there is a compensation layer and above the compensation layer there is a cover layer including a central aperture. The absorbent articles according to the present invention can also include a respective cover layer comprising an aperture. Finally, the absorbent article according to the present invention further includes an upper, liquid-permeable layer which is disposed towards the body when the article is used. The secondary storage layer can include at least one compressed region.

For example cellulose is a material suitable for the secondary storage layer. Local compressed regions in the secondary storage can for example be obtained by embossing grooves into the storage area. The storage material positioned underneath the embossed grooves is thus compressed and the grooves contribute to a directed liquid-distribution on the storage layer or in the absorbent article.

The cover layer including the central aperture is for example made from a mixture of cellulose and polymerised alkene. It is advantageous if the respective mixtures contain at least 50% by weight of polymerised alkene. Very good results are achieved if the content of polymerised alkene is 50–80% by weight, in particular 60% by weight. The cover layer may also be made from two layers, in such a way that a first layer made of cellulose and polymerised alkene is applied to a second carrier layer made of polymerised alkene. In this, the first layer made from a mixture of cellulose and polymerised alkene is connected to the liquid-impermeable layer which, when the article is used, is disposed towards the body, and the second carrier layer is connected to the compensation layer. Polyethylene, polypropylene and mixtures of polyethylene and polypropylene are preferred polymerised alkenes. Furthermore, the cover layer can include a pigment, such as for example titanium oxide. It is advantageous if the material of the compensation layer is made from a non-woven material. The non-woven material can include polymerised alkene and/or bicomponent fibres. The compensation layer on the surface disposed towards the storage layer can also be coated with a surface-active substance, which may for example contain silicon. The primary storage layer can for example include a UCTAD material (uncreped through air dried material), tissue cotton-wool or a polymeric alkene. It is advantageous if the primary storage layer is constructed in such a way that its marginal areas are folded in in such a way that they mutually overlap.

Both the liquid-impermeable layer and the liquid-permeable layer can be constructed from a polymerised alkene, such as for example polyethylene, polypropylene or a mixture thereof. For attachment of the absorbent article according to the invention to a garment, the liquid-impermeable layer may include at least one adhesion element and/or an adhesive layer. Furthermore, the absorbent article according to the invention may also include laterally arranged wings.

BRIEF DESCRIPTION OF THE DRAWINGS

The invention is explained in more detail below by means of the accompanying drawings in which:

FIG. 19 is a perspective view of a further embodiment of the absorbent article according to the invention, in the form of a sanitary napkin; and FIG. 20 is a cross-section through the absorbent article according to FIG. 19 along the line XX—XX.

DETAILED DESCRIPTION OF THE PRESENTLY PREFERRED EMBODIMENTS

Although the absorbent article according to the invention is shown below in detail in the form of sanitary napkins, it is evident that the present invention is not restricted to sanitary napkins for feminine hygiene but includes all absorbent hygiene articles.

Figure 1:
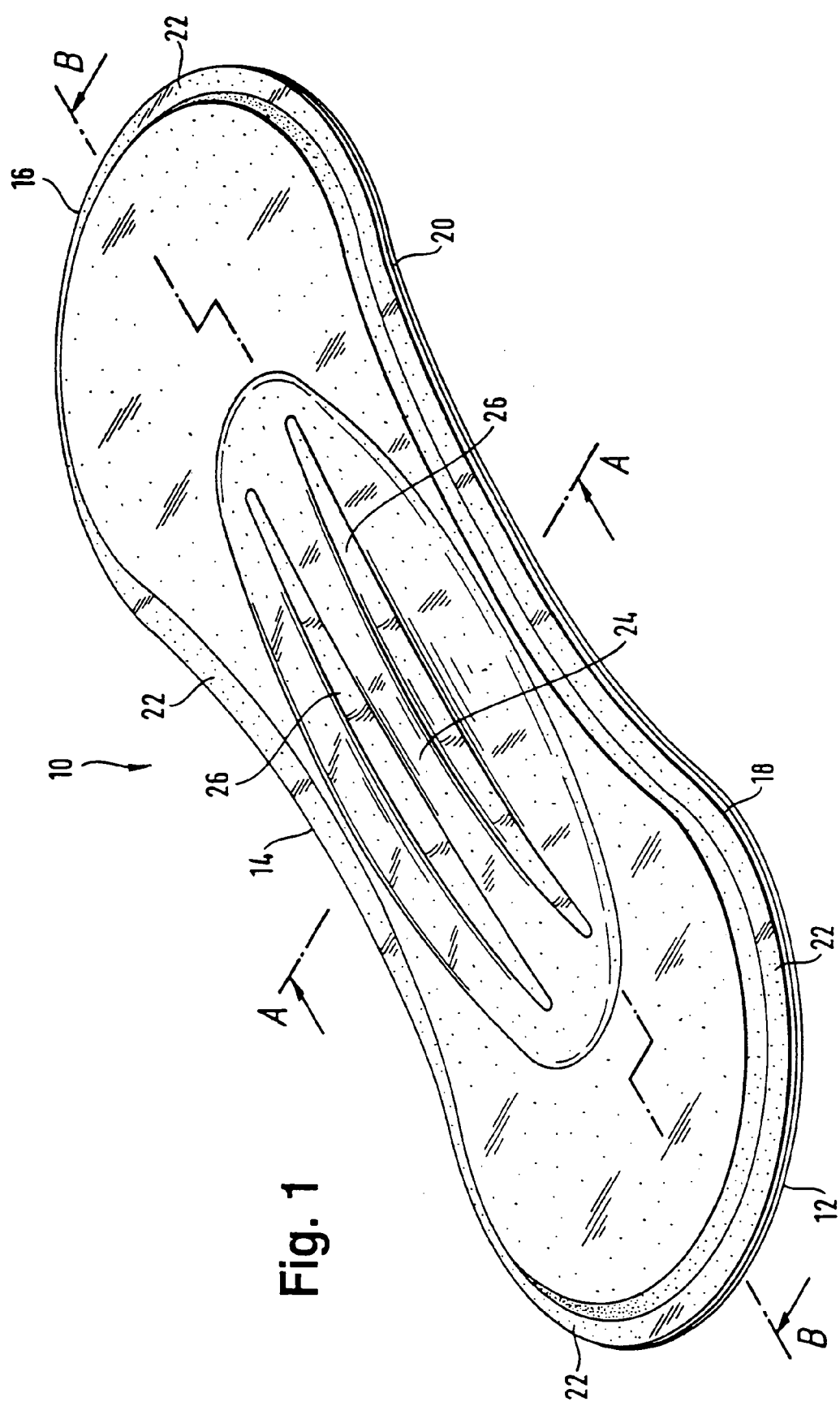
FIG. 1 is a perspective view of an absorbent article according to the invention in the form of a sanitary napkin.

FIG. 1 shows a sanitary napkin 10 according to the invention including a frontal region 12, a middle region 14 and a rear region 16. The liquid-permeable layer 18 disposed towards the wearer's body when the sanitary napkin 10 is in use, and the liquid-impermeable layer 20 disposed away from the wearer's body, are interconnected in the marginal area 22 of the sanitary napkin 10. In the centre, the absorbent body (not visible), extends in longitudinal direction of the sanitary napkin 10; the said absorbent body results in the liquid-permeable layer 18 in the centre of the sanitary napkin being raised in relation to the frontal region 12 and the rear region 16. Also visible are two longitudinal grooves 26 in the central region 24 which on the one hand reflect the chamber layout of the absorbent body and on the other hand contribute to directional liquid-distribution when the sanitary napkin is in contact with a liquid.

Figure 2:
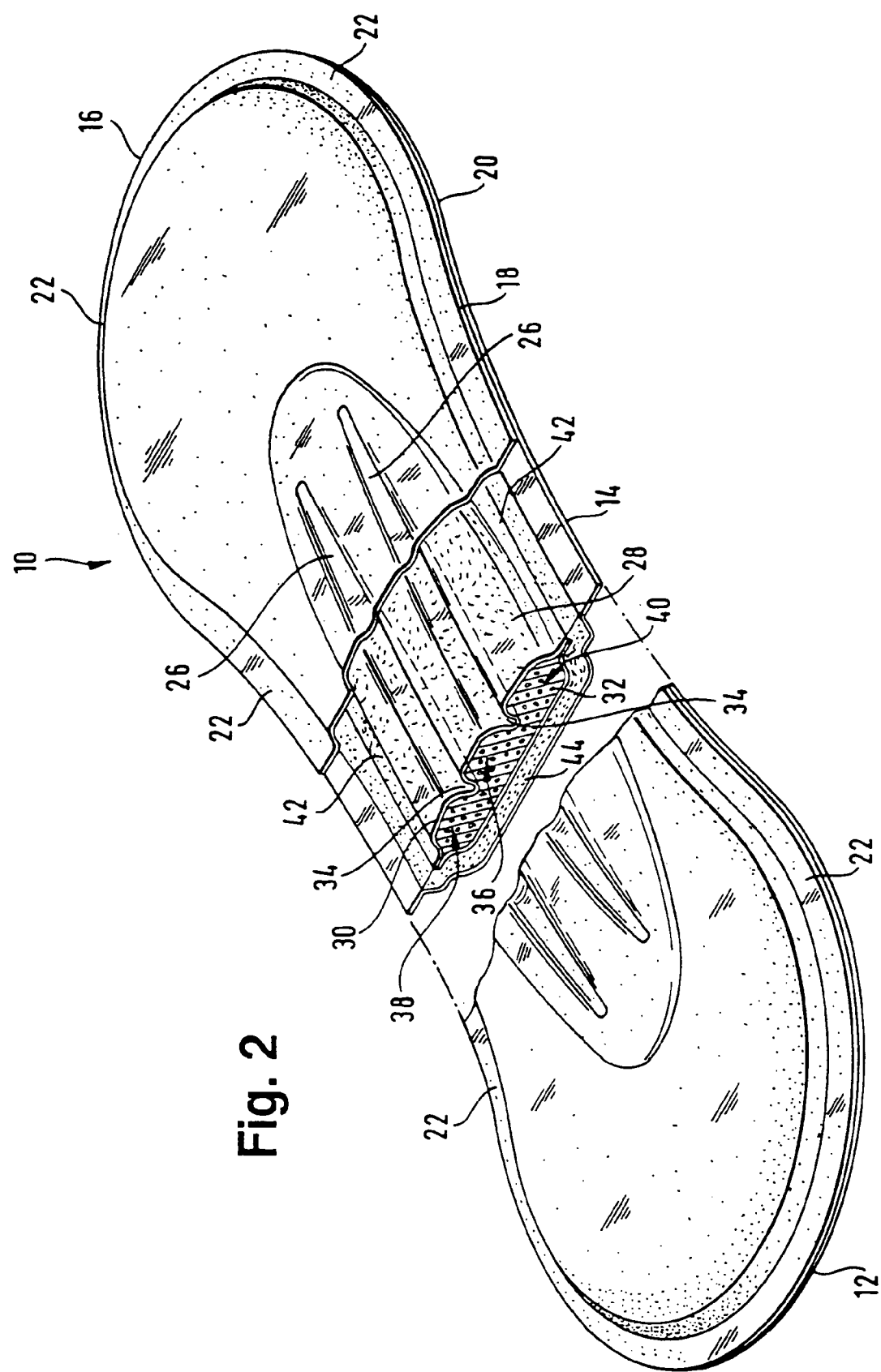
FIG. 2 is a perspective view of an absorbent article according to the invention in the form of a sanitary napkin, in partial section view.

FIG. 2 provides a perspective view of an absorbent article 10 according to the invention in partial section view. Shown again are the frontal region 12, the middle region 14 and the rear region 16 of the article. The liquid-permeable layer 18 and the liquid-impermeable layer 20 (garment protection film) are interconnected in the marginal area 22. The core 28 of the absorbent body of the article according to the invention is arranged in the central region of the said absorbent body and extends in longitudinal direction of the article. The core includes a (liquid-permeable) outer cover 30 made from a non-woven material. The material 32 which remains able to flow even after contact with a liquid, in the present case polymethylene urea with a particle size between 200 and 800 μm, is enclosed in the outer cover; the individual particles are largely spherical in shape. In the embodiment shown in FIG. 2, the outer cover 30 is almost entirely filled with material 32. This does not pose any problems because, even if contacted with a liquid, this material is not subject to moisture expansion (swelling) and there is thus no danger of the outer cover 30 bursting.

The longitudinal grooves 26 extend in longitudinal direction of the absorbent article 10. The outer cover 30 of the core includes tied-in areas 34 which cause a certain division into compartments of the absorbent material 32. In this, the core is divided into a central chamber 36 and lateral chambers 38, 40. As is clearly evident in FIG. 2, the delimitation walls of the individual chambers do not reach all the way to the base of the outer cover 30, so that a limited material exchange between individual chambers is possible. In the embodiment shown in FIG. 2, the outer cover 30 is made from two parts which are interconnected in the marginal area 42. This construction facilitates filling of the core with absorbent material.

In the embodiment of the article according to the invention shown in FIG. 2, the core 28, oval in shape, of the absorbent body, is also backed by an absorbent cellulose material 44. This cellulose material on the one hand contributes to wearer comfort, and on the other hand serves as reserve storage (secondary storage) in case the storage capacity of the core filled with polymethylene urea material, which remains able to flow even after having been in contact with a liquid, is exceeded. Normally, this reserve storage will however not have to be used since investigations show that for example the large majority of all sanitary napkins need to absorb less than 5 ml of liquid and for this the storage capacity of the core is adequate in every case.

When the article 10 according to the invention is in contact with blood, the blood is first of all distributed with the assistance of the longitudinal grooves 26. The blood then penetrates the liquid-permeable layer 18 and through the outer cover 30 enters the core 28 containing the material 32 where it is retained.

Figure 3:
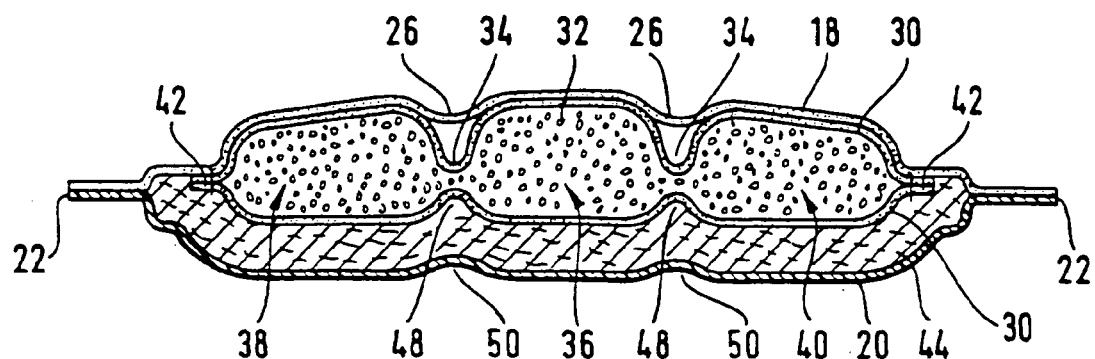
FIG. 3 is a cross-section through one embodiment of the absorbent article according to FIG. 1 along the line A—A of FIG. 1.

FIG. 3 shows a cross-section, along the line A—A in FIG. 1, through the absorbent article according to the invention. Viewed from top to bottom, under the liquid-permeable layer 18 of the core 28, the absorbent body can be seen. The core 28 is enclosed by the outer cover 30 and filled with the polymethylene urea material 32 which remains able to flow even after contact with a liquid. Below the core 28 there is a secondary storage layer made of cellulose material 44 (serving predominantly as a reserve or secondary storage), and the absorbent article is closed off below by the liquid-impermeable layer 20 which is made of polyethylene. A further special feature of the embodiment shown in FIG. 3 includes the outer cover 30 featuring tied-in areas 48 on the bottom too; the tied-in areas 48 being aligned with the tied-in areas 34 at the top. This results in a still more pronounced chamber layout of the core of the absorbent body, to a limited extent enabling material exchange between individual chambers. The liquid-permeable layer 18 and the liquid-impermeable layer 20 are interconnected in the marginal area 22. In the present case, this connection of the layers has been achieved by bonding the layers by an adhesive means. It is however also possible to interconnect the layers in other ways, for example by ultrasound or heat sealing. The two layers in the marginal area 42 of the outer cover 30 are bonded to each other in a similar way to that used in the marginal area 22.

Figure 4:
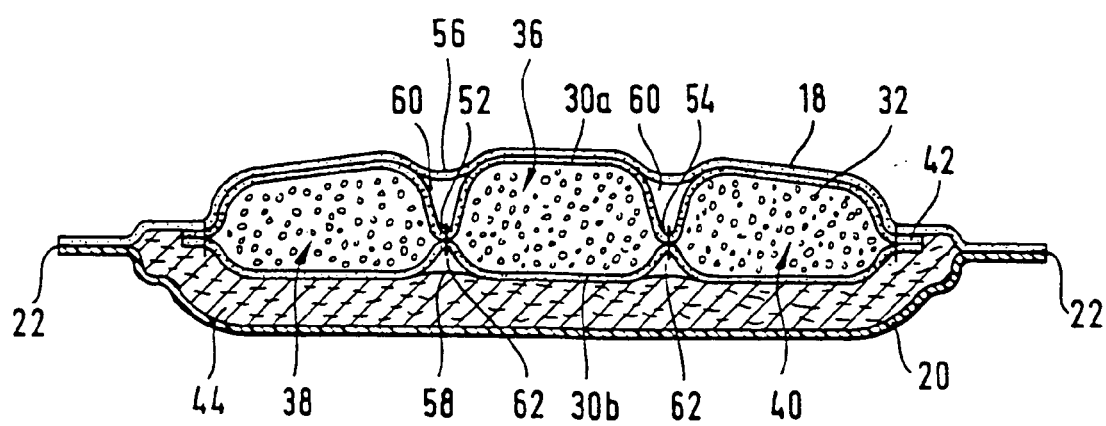
FIG. 4 is a cross-section through a further embodiment of an absorbent article according to the invention in the form of a sanitary napkin.

FIG. 4 shows a cross-section through a further embodiment of an absorbent article according to the invention. The same elements are described with the same reference numbers in FIGS. 3 and 4. In the embodiment according to FIG. 4, the lateral chambers 38, 40 are completely closed off from the central chamber 36 so that no exchange of material 32 is possible between the chambers. The chamber layout is achieved by the upper area 30a of the outer cover 30 and the lower area 30b of the outer cover 30 contacting each other at points 52, 54. A permanent connection is attained by sewing the upper or the lower outer cover layer. The chamber layout could for example also be achieved by bonding the upper area 30a to the lower area 30b. A further characteristic of the embodiment shown in FIGS. 3 and 4 consists of the presence of upper voids 60. The liquid which has entered can distribute itself very well in longitudinal direction in these voids, thus resulting in an even storage of the said liquid across the entire absorbent body. This arrangement allows optimal use of the absorption capacity and storage capacity of the core.

In FIG. 4, the reference number 58 indicates the upper edge of the secondary storage layer 44. If there are no indentations present in the liquid-impermeable layer 20, then small lower voids 62 can form between individual chambers of the absorbent body.

In addition, the absorbent body of the absorbent article according to the invention can also include a subdivision into chambers in such a way that there are subdivided areas (as shown in FIG. 4; compare numbers 52, 54) besides areas which allow a material exchange between chambers (as can be seen from FIG. 3, areas indicated by reference numbers between 34 and 48). This then leads to the formation of various areas, in longitudinal direction of the absorbent article, between the central chambers 36 and the lateral chambers 38, 40. In places, material exchange between chambers is possible (if the chambers are not completely separated from each other, as shown in FIG. 3); in other places material exchange is suppressed (as shown in FIG. 4, numbers 52, 54).

Figure 5:
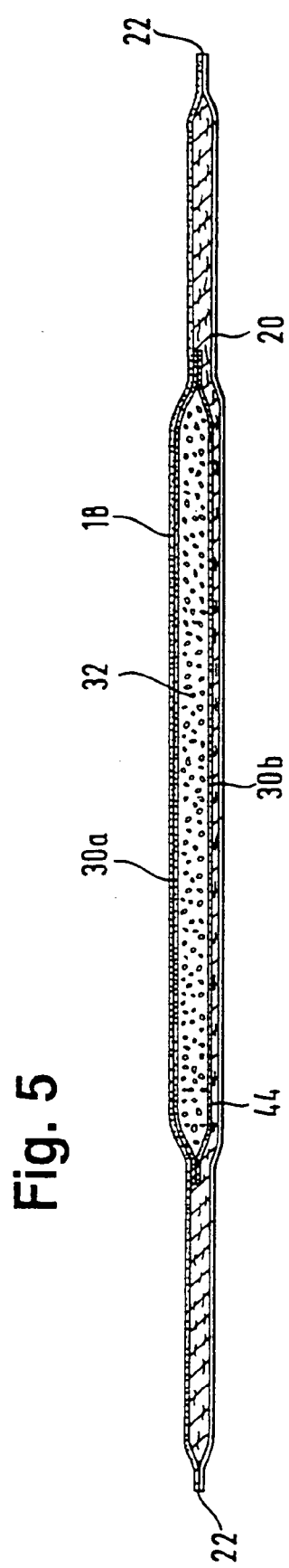
FIG. 5 is a longitudinal section through one embodiment of the absorbent article according to FIG. 1, along the line B—B of FIG. 1.

FIG. 5 is a longitudinal section through the absorbent article according to FIG. 1 along the line B—B in this figure. The liquid-permeable layer 18 and the liquid-impermeable layer 20 are interconnected in the marginal area 22. The central chamber of the core containing the polymethylene urea material 32, is also shown in longitudinal section view.

Figure 6:
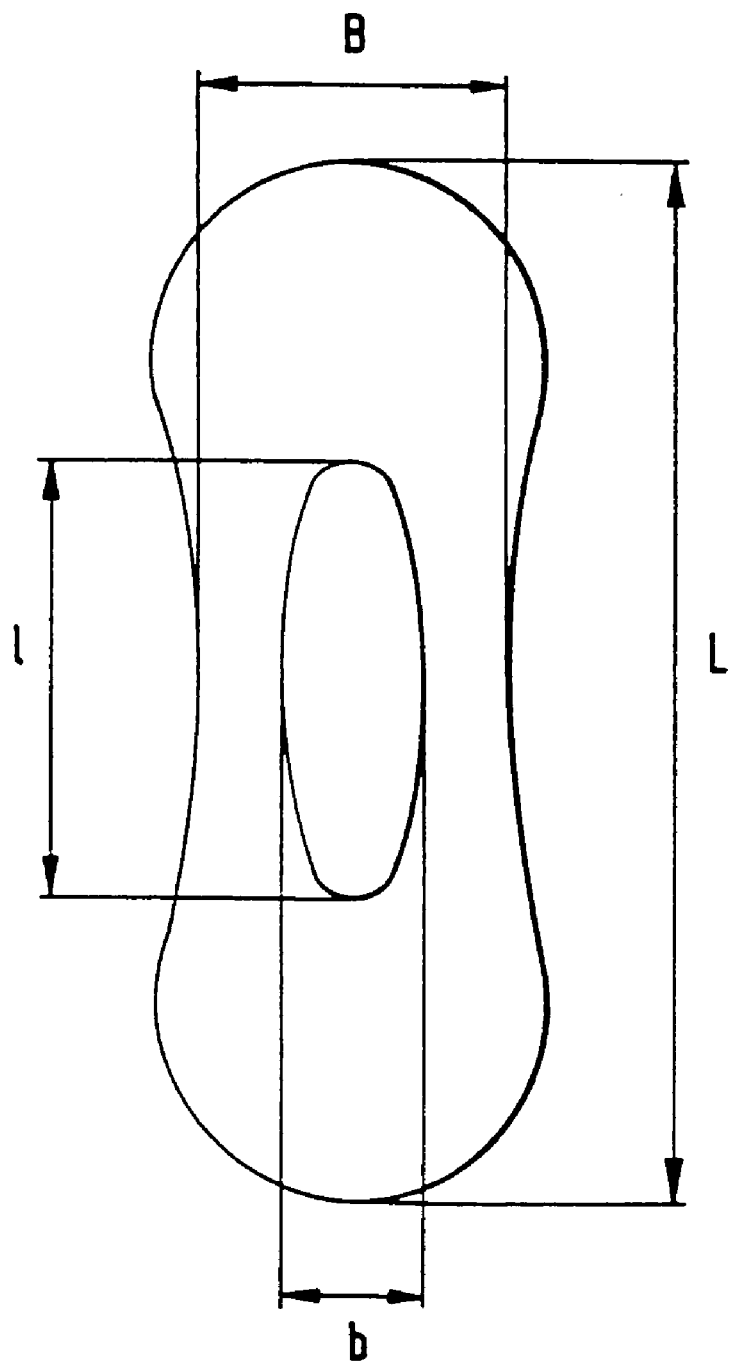
FIG. 6 is a diagrammatic view of the length and width ratios of an absorbent article according to the invention and a respective core of an absorbent element.

FIG. 6 shows how to favourably select the dimensions w and l of the core of the absorbent body in relation to the dimensions W and L of the absorbent article. It is advantageous in any case if w is smaller than W and l is smaller than L.

Figure 7:
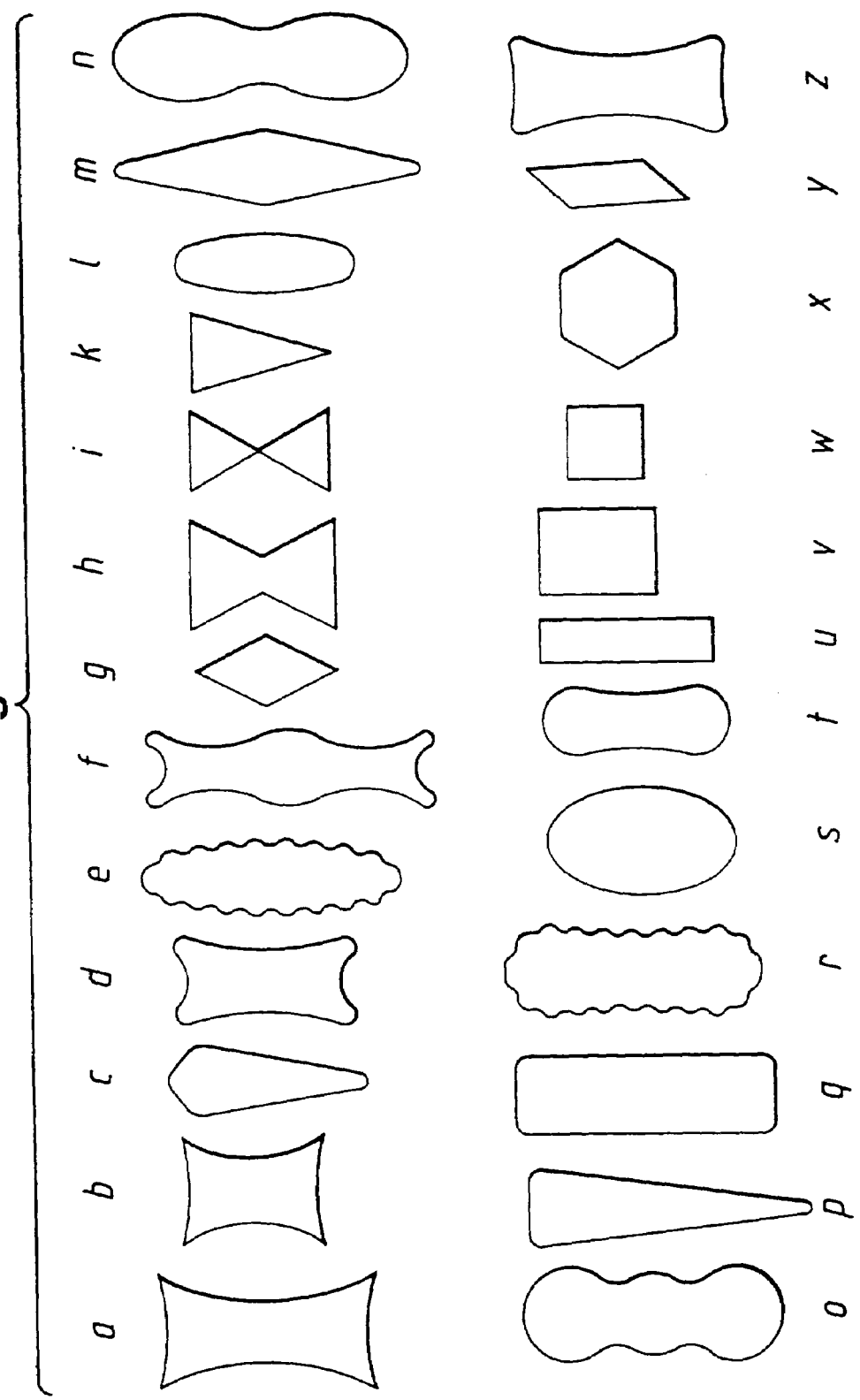
FIGS. 7a–z is a top view of shapes which the absorbent body or the core of the absorbent body of an absorbent article according to the invention, can assume.

FIGS. 7a to z shows 25 different possibilities of core design. Depending on the function of the absorbent article according to the invention, a suitable core can be selected. In the case of a "dog bone" structure, as shown in FIG. 1, it would be advantageous for example to use a similarly shaped core; see for example FIG. 6. But an oval shape (FIG. 7b) of the core can also be used to advantage (compare FIG. 1).

Figure 9:
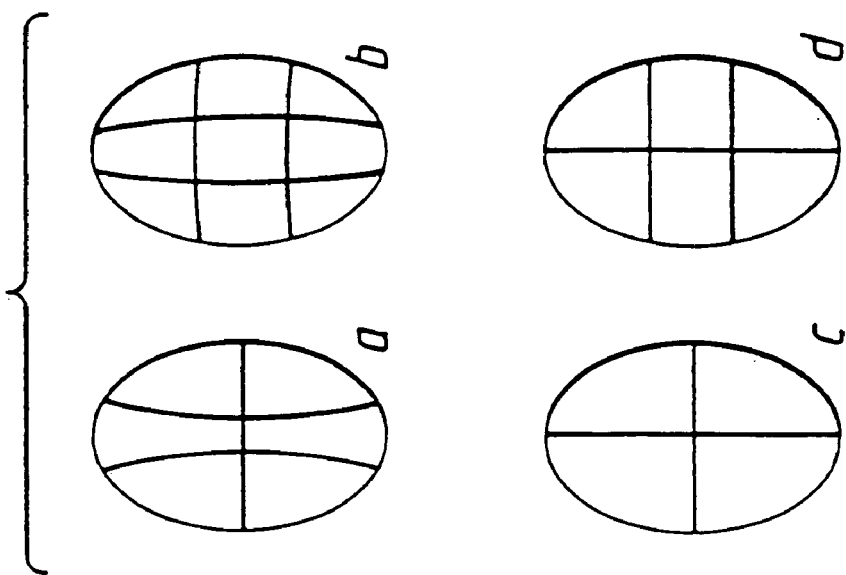
FIG. 9 is a view of the chamber layouts (in longitudinal and transverse directions) of the absorbent body or the core of the absorbent body of an article according to the invention.
Figure 8:
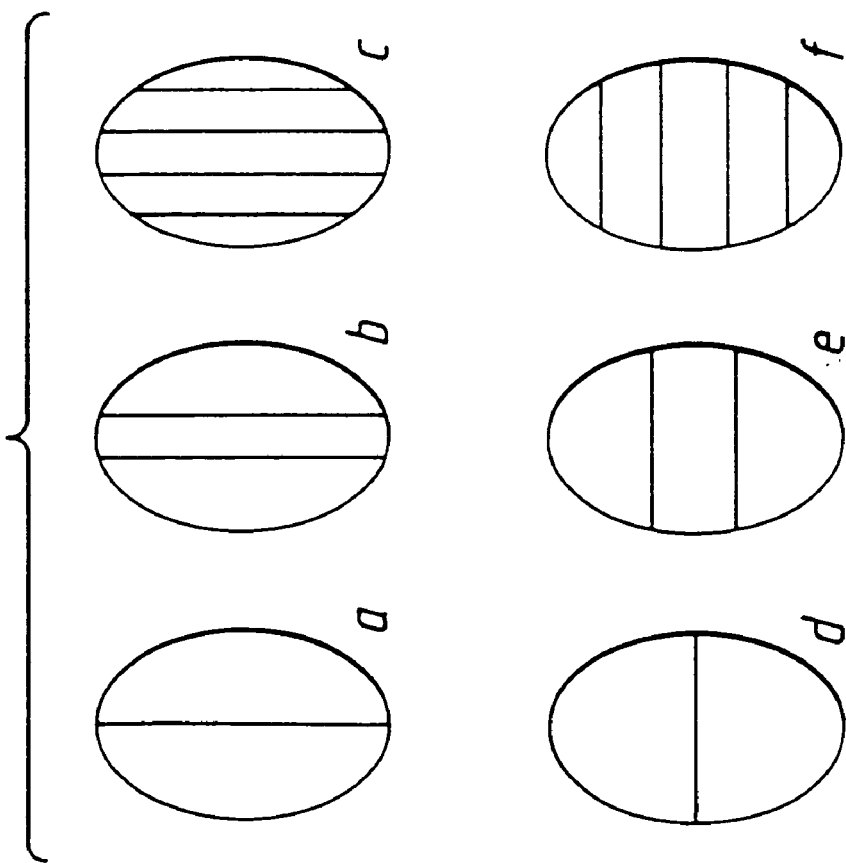
FIGS. 8a–c is a view of the chamber layouts (in longitudinal direction) of the absorbent body or the core of the absorbent body of an absorbent article according to the invention.
FIGS. 8d–f is a view of the chamber layouts (in transverse direction) of the absorbent body or the core of the absorbent body of an absorbent article according to the invention.

FIGS. 8 and 9 snow possibilities for subdividing (chamber layout) the core. The design shown in FIGS. 8a to c relates to longitudinal chambers, and embodiments according to FIGS. 8d to f relate to transverse chambers. FIG. 9 shows longitudinal and transverse chambers at the same time. The chamber design according to FIG. 8b corresponds to that shown in FIGS. 2 to 4.

FIG. 10 shows various deformations of the absorbent body under lateral pressure load and pressure load from above. In this, an oval core, shown in top view, can change to an hourglass or dog-bone shaped core (FIG. 10a) when lateral pressure forces are applied to the core by the wearer's thighs (compare arrows in the left diagram of FIG. 10a). The original width w1 (left diagram in FIG. 10a) in the step area is reduced to the width w2 (right diagram in FIG. 10a). This demonstrates the particular ability of the absorbent article according to the invention to fit very well to the anatomical contours of the wearer.

Figure 10A:
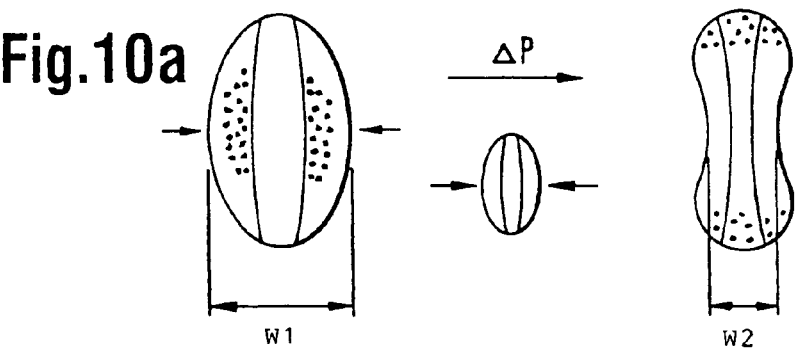
FIGS. 10a–d is a view of deformation possibilities of the absorbent body or the core of the absorbent body of an article according to the invention.
Figure 10B:
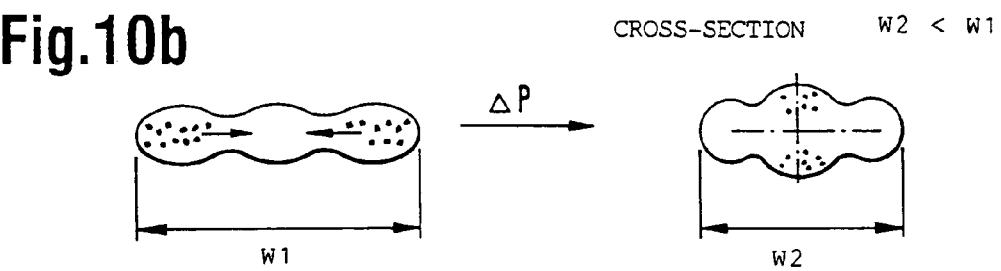

FIG. 10b shows the deformations illustrated in FIG. 10a of a core of an absorbent article in cross-section. This Fig. also shows clearly how absorbent material can be rearranged from the two laterally positioned chambers into the central chamber. The arrows indicate the direction of material movement.

FIG. 10a shows that during lateral pressure load, the outer shape and cross-sectional contours of the core area change but that the length l of the said core area essentially remains unchanged.

Figure 10C:
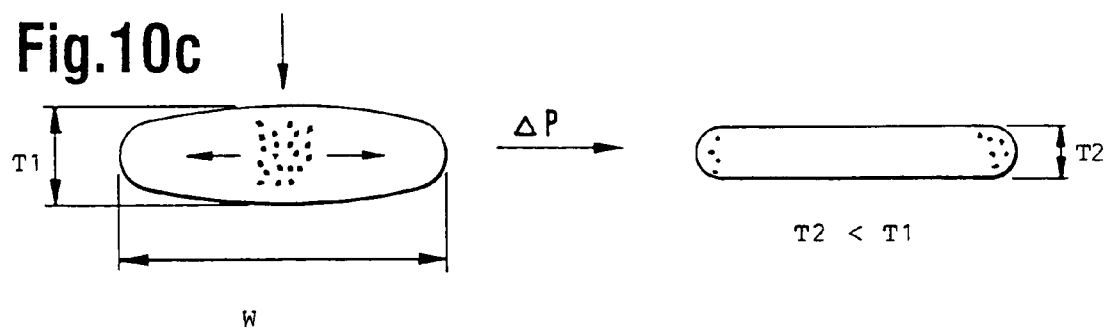

FIG. 10c shows the deformation of the core of the absorbent body during pressure load from above (arrow from above). It shows clearly how, by reducing the thickness of the core (D2<D1), material from the central region can be rearranged to lateral regions (arrows to the left and right). In this, the width w of the core remains essentially unchanged.

Figure 10D:
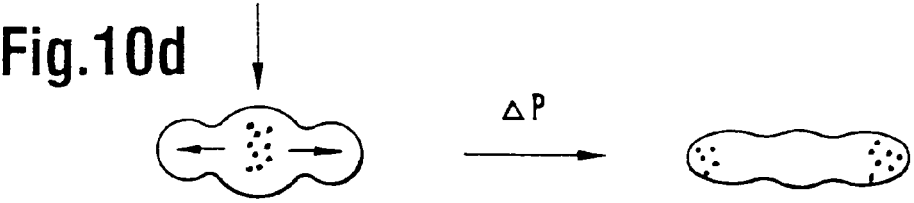

If the central core comprises a chamber layout as shown in FIG. 10d, then during pressure load from above (arrow from above) the thickness of the middle (central) chamber will be reduced and material will move to laterally located chambers, indicated by the arrows to the left and right (compare also FIG. 3).

Figure 11A:
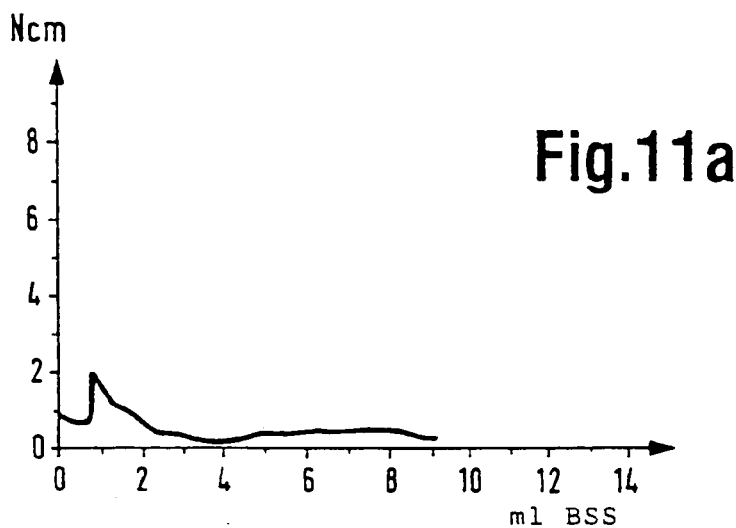
FIG. 11a shows the torque of a polymethylene urea powder during wetting with an increasing quantity of blood substitution solution (BSS)
Figure 11B:
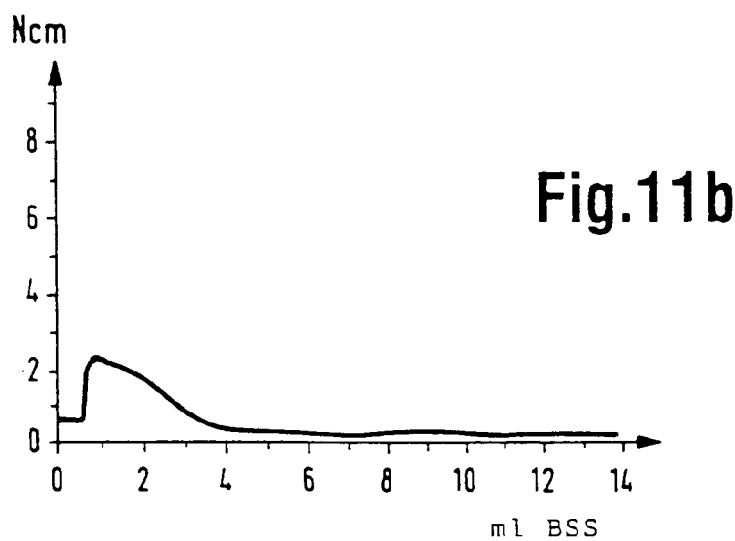
FIG. 11b shows the torque of a mixture of 8 parts by weight of polymethylene urea and 1 part by weight of polyacrylate (SAP) during wetting with an increasing quantity of blood substitution solution (BSS)
Figure 11C:
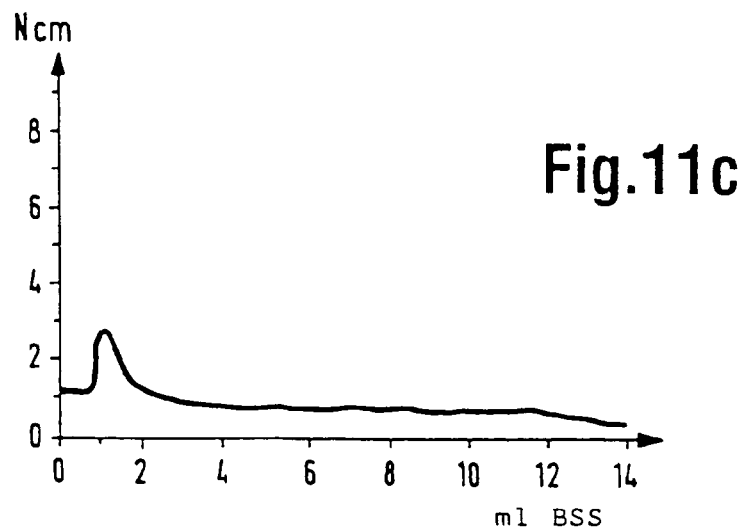
FIG. 11c shows the torque of a mixture of 4 parts by weight of polymethylene urea and 1 part by weight of polyacrylate (SAP) during wetting with an increasing quantity of blood substitution solution (BSS)
Figure 11D:
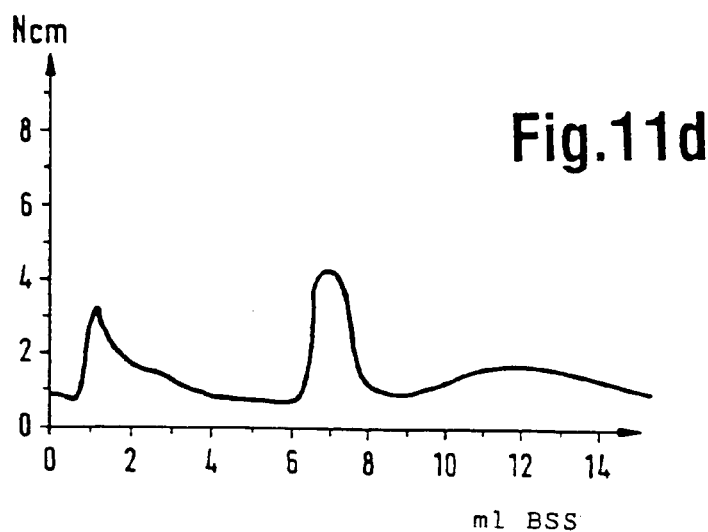
FIG. 11d shows the torque of a mixture of 2 parts by weight of polymethylene urea and 1 part by weight of polyacrylate (SAP) during wetting with an increasing quantity of blood substitution solution (BSS)
Figure 11E:
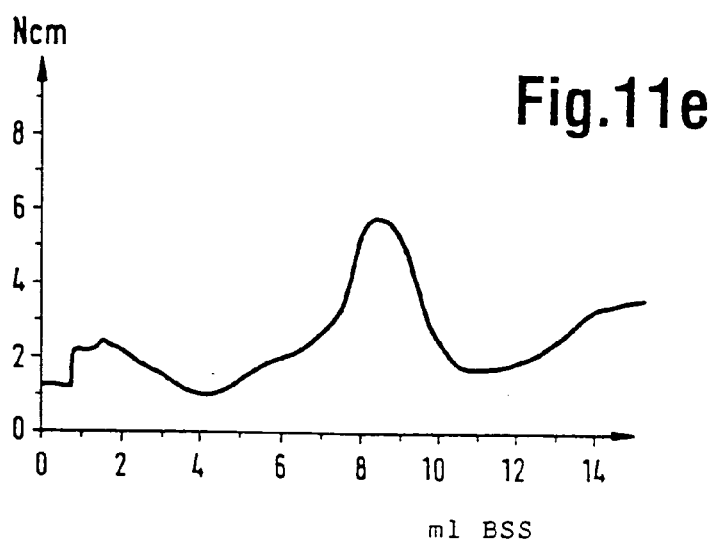
FIG. 11e shows the torque of a mixture of equal parts by weight of polymethylene urea and polyacrylate (SAP) during wetting with an increasing quantity of blood substitution solution (BSS)
Figure 11F:
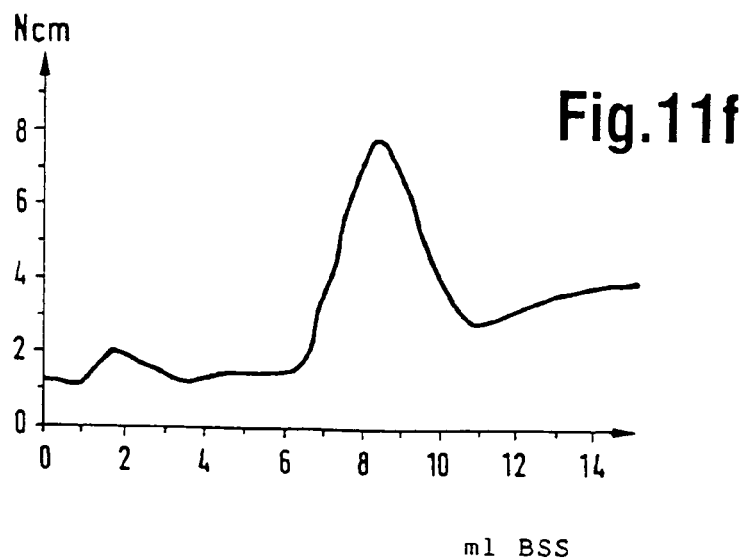
FIG. 11*f* shows the torque of a mixture of 1 part by weight of polymethylene urea and 2 parts by weight of polyacrylate (SAP) during wetting with an increasing quantity of blood substitution solution (BSS)

FIGS. 11e to f shows the torque (in Ncm) when stirring polymethylene urea powder or polymethylene urea/polyacrylate (superabsorber) mixtures with the addition of certain quantities of blood substitution solution (BSS). FIG. 11a illustrates pure polymethylene urea and shows a maximum of approx. 2 Ncm at approx. 1 ml BSS. Similar conditions result with 8 parts by weight of polymethylene urea to 1 part by weight of polyacrylate (SAP) as shown in FIG. 11b and with a mixture of 4 parts by weight of polymethylene urea and 1 part by weight of polyacrylate (SAP) (FIG. 11c), with the maximum rising slightly at 1 ml BSS (FIG. 11b approx. 2.4 Ncm and FIG. 11c approx 2.8 Ncm).

When examining mixtures comprising 2 parts by weight of polymethylene urea and 1 part by weight of polyacrylate (SAP), then it becomes evident that the 1 ml maximum rises to approx. 3.2 Ncm, and a second maximum of approx. 4.2 Ncm occurs at approx. 7 ml BSS (FIG. 11d). With a mixture of equal parts by weight of polymethylene urea and polyacrylate (SAP), a first maximum of approx. 2.5 Ncm occurs at about 1.8 ml BSS, and a second maximum of approx. 6 Ncm occurs at approx. 8.3 ml BSS (FIG. 11e). With a mixture containing 1 part by weight polymethylene urea and 2 parts by weight polyacrylate (SAP), this second maximum rises to approx. 8 Ncm at approx. 8.3 ml BSS (FIG. 11f).

It is evident from the data shown in FIGS. 11a to f that (after overcoming a first maximum at approx. 1 ml liquid-supply) pure polymethylene urea and mixtures of up to 4 parts per weight of polymethylene urea with 1 part by weight SAP can be supplied with larger quantities of BSS (up to 14 ml) without a significant friction resistance of the particles of absorbent material resulting. This is an important indicator for the high wearer comfort of the absorbent articles containing the respective materials as an absorbent. Since most sanitary napkins for feminine hygiene, as has been mentioned before, do not have to absorb more than 5 ml liquid, the pronounced second maximum, which occurs in mixtures containing less than 2 parts by weight of polymethylene urea per part by weight of SAP, does not have any negative effect.

Figure 12:
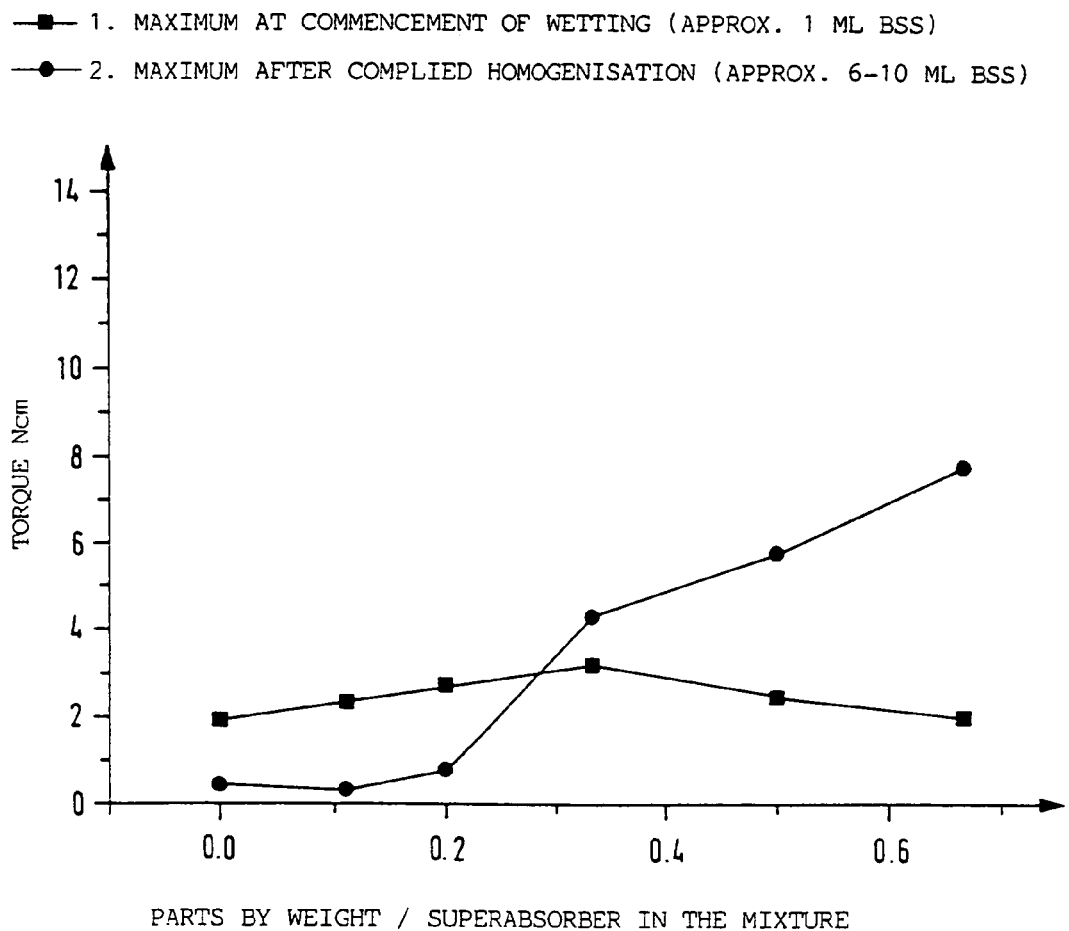
FIG. 12 is a diagram illustrating the maximum torques of polymethylene urea or various mixtures of polymethylene urea/SMH during wetting with a blood substitution solution (BSS)

Finally, FIG. 12 shows the maximum torque in Ncm at commencement of wetting with BSS and after completed homogenisation of polymethylene urea/polyacrylate (SAP) mixtures.

Figure 13:
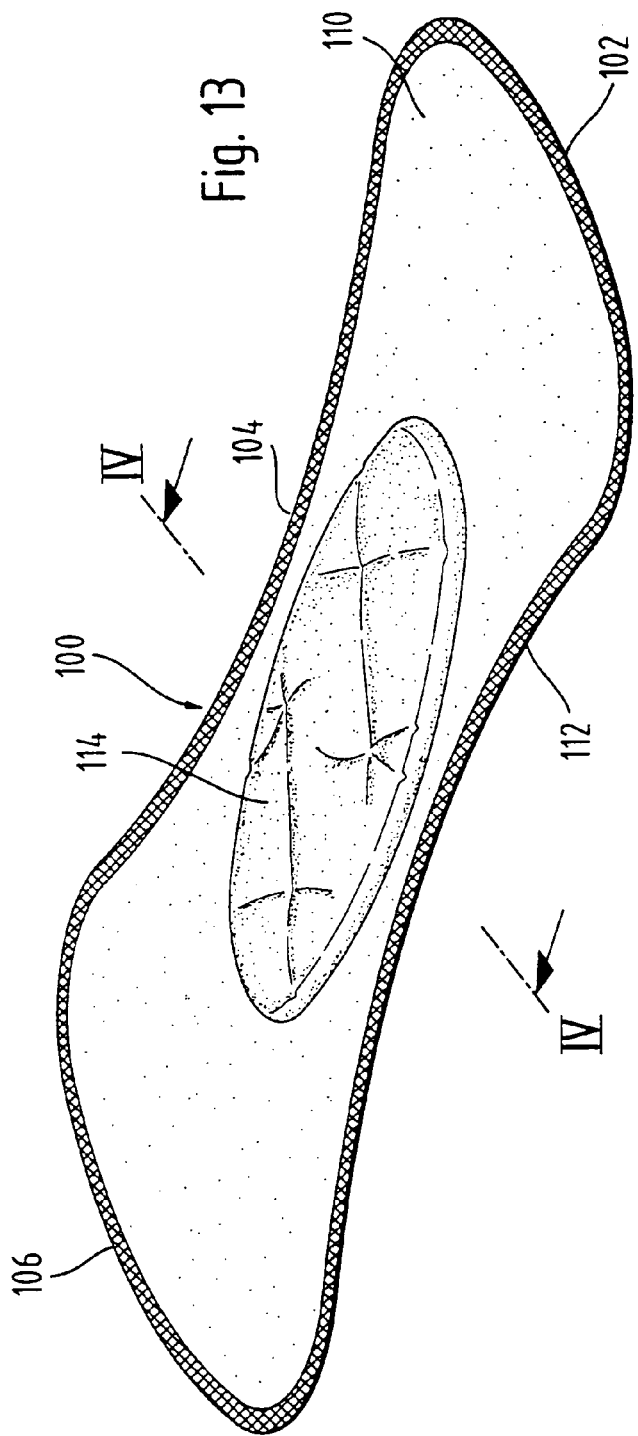
FIG. 13 is a perspective view of a further absorbent article according to the invention in the form of a sanitary napkin.

FIG. 13 shows a sanitary napkin 100 of the invention, comprising a frontal region 102, a middle region 104 and a rear region 106. A layer 110 made from a soft coform material is applied to a liquid-impermeable layer (not shown in FIG. 13). The layer 110 is connected to the supporting liquid-impermeable layer by an adhesive means 118. In the marginal area, the two layers are additionally connected to each other by thermal-mechanical means or by ultrasound. On the one hand, the layer 110 serves to increase the wearer comfort of the absorbent article by its softness; on the other hand, the layer 110 can also serve as a reserve or secondary storage if liquid to be absorbed reaches the marginal areas of the absorbent article. The layer 110 comprises a central absorbent body and storage body 114. The absorbent body comprises a liquid-permeable outer cover. The outer cover comprises a liquid absorbent material which remains able to flow even after contact with a liquid.

Figure 14:
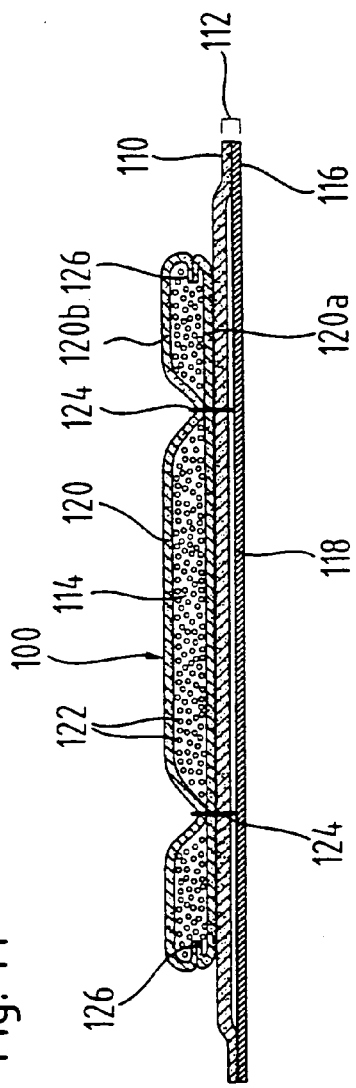
FIG. 14 is a cross-section through the absorbent article according to FIG. 13 along the line IV—IV.

FIG. 14 shows in detail the structure of the absorbent article according to the invention according to FIG. 13, with FIG. 14 showing a cross-section along line IV—IV shown in FIG. 13. FIG. 14 shows the liquid-impermeable rear cover layer 116 made from polyethylene. On the one hand, the cover layer 116 serves as a support for the overlaying layers (arranged in closer proximity to the wearer's body) of the absorbent article. On the other hand the cover layer 116 serves as a garment protection film which protects the wearer's undergarments from soiling by bodily fluids. In the marginal area 112, the liquid-impermeable layer 116 and the layer 110 made from a soft coform material, are stamped together. The absorbent body 114 is attached to the layer 110. The absorbent body 114 comprises an outer cover 120 made from a non-woven material which comprises a material 122 which remains able to flow even after contact with a liquid, namely polymethylene urea in spherical shape with a particle diameter ranging between 200 and 800 μm. The outer cover 120 is connected to the layer 110 by means of seams 124. On the one hand, the seams 124 cause the layer 110 to be held to the absorbent body 114 and on the other hand also cause a certain division into compartments of the absorbent body 114. In this, as a result of the seams 124, in the absorbent body according to the embodiment shown in FIGS. 13 and 14, the absorbent body is not divided into two or more completely separate regions because the seams are not arranged right through. The type of stitching used to attach the absorbent body 114 to the coform layer 110, shown in FIG. 14, ensures that the supporting liquid-impermeable layer 116 remains intact and can fulfil its function as a garment protection film. The absorbent body 114 comprises marginal areas 126 where a section 120a of the outer cover 120 facing the coform layer, is connected by an adhesive means to a section 120b of the outer cover 120 facing the body. Prior to filling the absorbent body 114 with the absorbable material 122 with storage properties, the sections 120a and 120b are first partly connected to each other in such a way that a filling aperture remains. Subsequently, the material 122 is fed in through the filling aperture, up to the desired degree of filling; in the present case 80% of the theoretical total filling capacity; and subsequently the areas 120a and 120b are also connected to each other in the filling aperture section, resulting in the completed absorbent body 114 which is subsequently fixed by means of stitches to the coform layer 110.

The advantage of the absorbent article 100 according to the invention as shown in FIGS. 13 and 14, when compared to traditional absorbent articles can be found in that on the one hand the absorbent body and the absorbent material contained therein are very easily accessible because only the outer cover is between the absorbent material and the wearer's body; and on the other hand the unrestricted and exposed position of the absorbent body makes it possible for the said absorbent body to optimally adapt to the anatomical contours of the wearer. In this way, the article according to the invention ensures very high wearer comfort.

Figure 15:
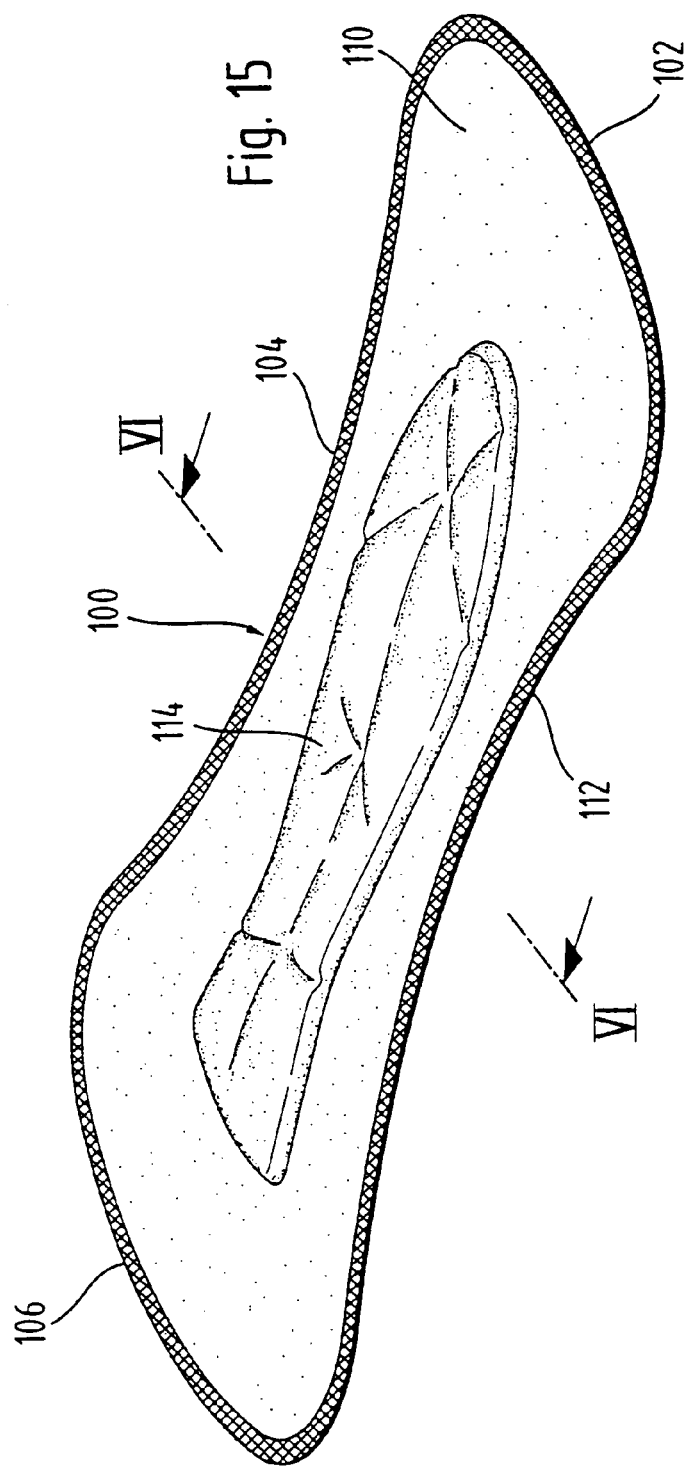
FIG. 15 is a perspective view of a further absorbent article according to the invention in the form of a sanitary napkin.
Figure 16:
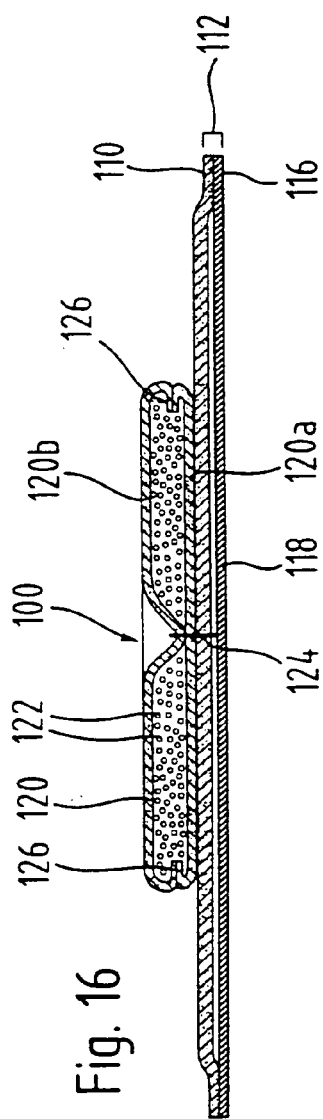
FIG. 16 is a cross-section through the absorbent article according to FIG. 15 along the line VI—VI.

FIGS. 15 and 16 also show a sanitary napkin which in principle has the same design as the embodiments shown in FIGS. 13 and 14, with the embodiment in FIG. 16 showing a cross-section through the article along the line VI—VI in FIG. 15. The reference numbers in FIGS. 15 and 16 correspond to those in FIGS. 13 and 14. Similarly, the materials described in conjunction with FIGS. 13 and 14 correspond to those in FIGS. 15 and 16. As can be seen from the perspective views in FIGS. 13 and 15, the embodiments according to FIGS. 13 and 15 differ in the shape of the absorbent body 114. Whereas the absorbent body 114 according to FIG. 13 is of elongated oval shape, the absorbent body according to FIG. 15 is of elongated lanceolate shape. This increase in size of the absorbent body further increases the liquid-absorption capacity of the absorbent article according to the invention. As can be seen from FIG. 16, the absorbent body 114 is connected to its underlying layer 110 merely by a central seam 124 whereby the adaptability of the absorbent body 114 to various wearer situations is still further improved.

Figure 17:
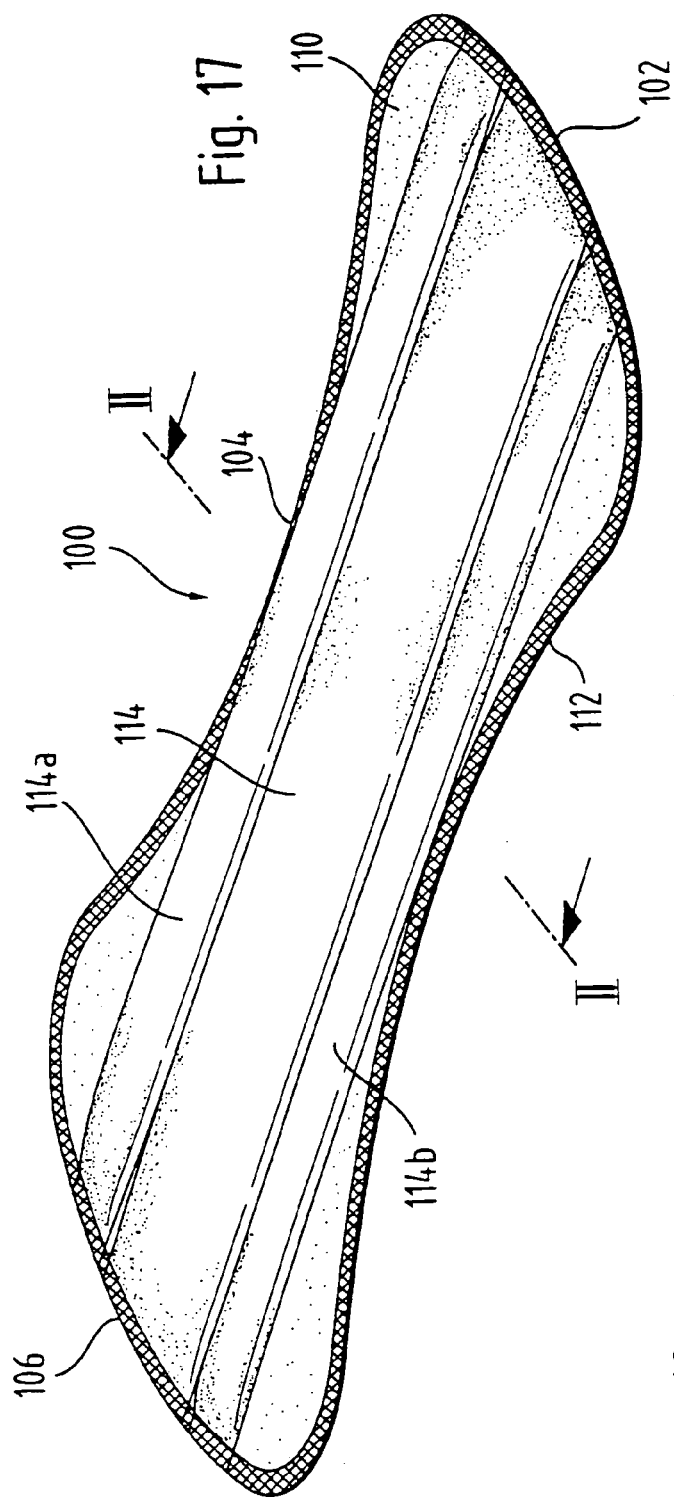
FIG. 17 is a perspective view of a further absorbent article according to the invention in the form of a sanitary napkin.
Figure 18:
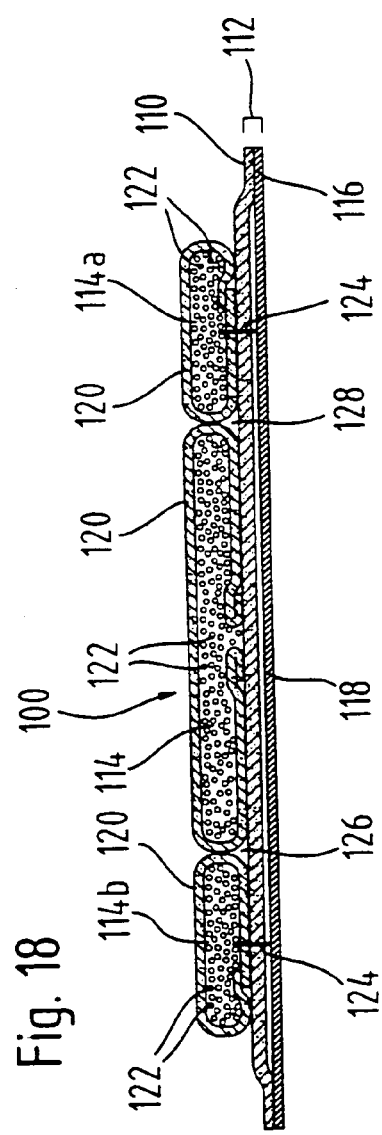
FIG. 18 is a cross-section through the absorbent article according to FIG. 17 along the line II—II.

FIGS. 17 and 18 finally show a further modification of the absorbent article according to the invention, with FIG. 17 showing a perspective view and FIG. 18 a view along the line II—II in FIG. 17. The reference numbers used in FIGS. 13 and 14 denote corresponding components in FIGS. 17 and 18. The materials described in conjunction with FIGS. 13 and 14 also correspond to those in FIGS. 17 and 18.

The special feature of the embodiment shown in FIGS. 17 and 18 of an absorbent article according to the invention consists of the division into three parts of the absorbent body into a central section 114 and two lateral sections 114a and 114b. As can be seen in FIG. 18, the absorbent body comprises three sections 114, 114a and 114b of the absorbent body which sections are completely separate from each other. Channels 126, 128 aligned in longitudinal direction are arranged between the central absorbent body 114 and the lateral absorbent bodies 114a and 114b. This embodiment of the absorbent article according to the invention ensures particularly good leakage protection because, if the central absorbent body 114 should "spill over", there are still the lateral absorbent bodies 114a, 114b available for liquid absorption. This type of absorbent article is thus particularly suitable for situations in which large quantities of liquid need to be absorbed and stored in a relatively short period of time. In this, the channels 126, 128 support distribution of the liquid in longitudinal direction of the absorbent article, i.e. the total available capacity for absorption and storage is used even more effectively because in close proximity to the central contact area, even marginal areas and terminal areas of the absorbent body can be used optimally for liquid storage.

A further special embodiment of the absorbent article according to the invention is shown in FIGS. 19 and 20. Again, the article is a sanitary napkin, shown in perspective view in FIG. 19 and in cross-section in FIG. 20. The article comprises a liquid-impermeable layer 116, made of polyethylene, which is disposed away from the wearer's body when the said article is in use. Arranged on this layer 116 is a layer 110 made of soft coform material which on the one hand serves to increase the wearer comfort of the article. On the other hand, this layer 110 can also serve as reserve storage or secondary storage which absorbs and stores liquid not absorbed and retained in the absorbent body 114.

The absorbent body 114 in turn is surrounded by a liquid-permeable layer or outer cover 120 made from a non-woven material. The liquid-absorbent and liquid-storing material 122 in the absorbent body 114 is polymethylene urea material free from ether groups and free from formaldehyde groups, whereby the absorbent body is filled with the polymethylene urea material up to 70% of its theoretical capacity. This degree of filling ensures very good adaptability of the article to the wearer's body contours.

The absorbent body 114 is connected to the layer 110 underneath it and via this layer with the liquid-impermeable layer 116 by way of a seam or of adhesion 124. The reference number 112 designates the marginal area connecting the layers 110 and 116.

The embodiment shown in FIGS. 19 and 20 is characterized by the arrangement of the liquid-permeable cover layer 130.

This cover layer comprises folds, marked with the reference number 132, which extend in longitudinal direction of the article. The folding of the layer 130 extends underneath the absorbent body 114 up to a further folding 134 from where the cover layer again extends in the direction of the margin of the article. Between the folding 134 and the marginal area of the article, the layer 130 is connected by means of adhesion with the underlying layer 110. This special arrangement of the cover layer 130 ensures good mobility and adaptability of the absorbent body and of the entire article to the wearer's body contours.

What is claimed is:

1. An absorbent article, comprising:
a liquid-permeable layer,
a substantially liquid-impermeable layer; and
an absorbent body between the liquid-permeable layer and the substantially liquid-impermeable layer;
the absorbent body comprising an absorbent material which absorbs 10 ml or more of water per gram of absorbent material and absorbs said water under conditions where no volume expansion is possible.

2. The absorbent article of claim 1, wherein the absorbent material comprises absorbent particles.

3. The absorbent article of claim 2, wherein the absorbent particles comprise spherical particles.

4. The absorbent article of claim 2, wherein the absorbent particles have a diameter of about 100–2000 microns.

5. The absorbent article of claim 2, wherein the absorbent particles have a diameter of about 200–800 microns.

6. The absorbent article of claim 1, wherein the absorbent material comprises polymethylene urea.

7. The absorbent article of claim 6, wherein the polymethylene urea constitutes at least about one third by weight of the absorbent material.

8. The absorbent article of claim 6, wherein the polymethylene urea constitutes at least about one half by weight of the absorbent material.

9. The absorbent article of claim 6, wherein the polymethylene urea constitutes at least about two thirds by weight of the absorbent material.

10. The absorbent article of claim 6, wherein the polymethylene urea constitutes at least about 80% by weight of the absorbent material.

11. The absorbent article of claim 6, wherein the absorbent material consists essentially of the polymethylene urea.

12. The absorbent article of claim 6, wherein the polymethylene urea is substantially free of ether groups and formaldehyde.

13. The absorbent article of claim 1, wherein the absorbent material comprises a superabsorbent material.

14. The absorbent article of claim 13, wherein the superabsorbent material comprises a polyacrylate.

15. The absorbent article of claim 1, wherein the absorbent body further comprises a fibrous matrix, and the absorbent material is disposed within the matrix.

16. The absorbent article of claim 1, wherein the absorbent body further comprises at least one care substance.

17. The absorbent article of claim 16, wherein the care substance comprises a material selected from extracts of aloe vera, marigold, chamomile, and combinations thereof.

18. The absorbent article, comprising:
a substantially liquid-impermeable layer;
an absorbent body connected to the substantially liquid-impermeable layer in a central region of the substantially liquid-impermeable layer; and
a liquid permeable layer over a side of the absorbent body opposite the substantially liquid-impermeable layer;
the absorbent body comprising an absorbent material which absorbs 10 ml or more of water per gram of absorbent material and absorbs said water under conditions where no volume expansion is possible.

19. The absorbent article of claim 18, wherein the absorbent body and substantially liquid-impermeable layer are connected using an adhesive.

20. The absorbent article of claim 18, wherein the absorbent body and substantially liquid-impermeable layer are connected using one or more seams.

21. The absorbent article of claim 18, wherein the absorbent body further comprises a secondary storage layer including a soft absorbent material.

22. The absorbent article of claim 21, wherein the soft absorbent material comprises a material selected from coform materials, airlaid materials, tissue cotton-wools, and combinations thereof.

23. The absorbent article of claim 21, wherein the soft absorbent material comprises a nonwoven material selected from spunbond fabrics, carded webs, and combinations thereof.

24. The absorbent article of claim 18, wherein the absorbent body further comprises a fibrous matrix, and the absorbent material is disposed within the matrix.

25. The absorbent article of claim 24, wherein the absorbent material is disposed substantially homogeneously within the matrix.

26. The absorbent article of claim 18, wherein the absorbent body further comprises two or more layers of a fibrous material, and the absorbent material is disposed between the layers of fibrous material.

27. The absorbent article of claim 24, wherein the fibrous matrix comprises a material selected from cellulose, a cellulose/polypropylene mixture, a coform material, and combinations thereof.

28. The absorbent article of claim 26, wherein the two or more layers of fibrous material comprise a material selected from cellulose, a cellulose/polypropylene mixture, a coform material, and combinations thereof.

29. The absorbent article of claim 24, wherein the absorbent body comprises the fibrous material and absorbent material in a weight ratio of about 99–75% fibrous material to about 1–25% absorbent material.

30. The absorbent article of claim 29, wherein the weight ratio is about 95–80% fibrous to about 5–20% absorbent material.

31. The absorbent article of claim 29, wherein the weight ratio is about 90–85% fibrous material to about 10–15% absorbent material.

32. The absorbent article of claim 18, wherein the absorbent body further comprises at least one care substance.

33. The absorbent article of claim 32, wherein the care substance comprises a material selected from extracts of aloe vera, marigold, chamomile, and combinations thereof.

34. The absorbent article of claim 32, wherein the care substance is enclosed in microcapsules.

35. The absorbent article of claim 34, wherein the care substance is releasable from the microcapsules in response to heat or pressure.

36. The absorbent article of claim 18, wherein the absorbent material is treated with a substance selected from bactericidal, fungicidal and viricidal substances, and combinations thereof.

37. The absorbent article of claim 36, wherein the substance comprises a bactericidal substance selected from chlorinated levulinic acid, alkyldimethylbenzylammonium halogenides, and combinations thereof.

38. The absorbent article of claim 18, wherein the absorbent material comprises absorbent particles.

39. The absorbent article of claim 38, wherein the absorbent particles comprise spherical particles.

40. The absorbent article of claim 38, wherein the spherical particles have a diameter of about 100–200 microns.

41. The absorbent article of claim 38, wherein the spherical particles have a diameter of about 200–800 microns.

42. The absorbent article of claim 18, wherein the absorbent material comprises polymethylene urea.

43. The absorbent article of claim 42, wherein the polymethylene urea constitutes at least one third of the absorbent material.

44. The absorbent article of claim 42, wherein the polymethylene urea constitutes at least one half of the absorbent material.

45. The absorbent article of claim 42, wherein the polymethylene urea constitutes at least two thirds of the absorbent material.

46. The absorbent article of claim 42, wherein the polymethylene urea constitutes at least 80% of the absorbent material.

47. The absorbent article of claim 42, wherein the absorbent material consists essentially of the polymethylene urea.

48. The absorbent article of claim 42, wherein the polymethylene urea is substantially free of ether groups and formaldehyde.

49. The absorbent article of claim 18, wherein the absorbent material comprises a superabsorbent material.

50. The absorbent article of claim 49, wherein the superabsorbent material comprises a polyacrylate.

51. The absorbent article of claim 18, having a length and a width, wherein the absorbent body comprises at least one core which contains the absorbent material, the core having a length that is less than or equal to the length of the absorbent article, and a width that is less than or equal to the width of the absorbent article.

52. The absorbent article of claim 18, wherein the absorbent body comprises at least two chambers, and at least one wall between the chambers.

53. The absorbent article of claim 52, wherein the wall is aligned in a longitudinal direction of the absorbent article.

54. The absorbent article of claim 52, wherein the wall is aligned in a transverse direction of the absorbent article.

55. The absorbent article of claim 52, comprising at least one wall aligned in a longitudinal direction of the absorbent article and at least one wall aligned in a transverse direction of the absorbent article.

56. The absorbent article of claim 51, wherein the core comprises a plurality of chambers.

57. A hygiene article, comprising:
a liquid-permeable layer;
a substantially liquid-permeable layer; and
an absorbent body between the liquid-permeable layer and the substantially liquid-impermeable layer;
the absorbent body comprising an absorbent material which absorbs 10 ml or more of water per gram of absorbent material and absorbs said water under conditions where no volume expansion is possible.

58. The hygiene article of claim 57, comprising a feminine hygiene article.

59. The hygiene article of claim 57, comprising a sanitary napkin.

60. The hygiene article of claim 57, comprising a panty liner.

61. The hygiene article of claim 57, wherein the liquid-permeable layer comprises a central aperture.

62. The absorbent article of claim 1, comprising a diaper.

63. The absorbent article of claim 1, comprising an incontinence pad.

64. The absorbent article of claim 18, comprising a feminine hygiene article.

65. The absorbent article of claim 18, comprising a diaper.

66. The absorbent article of claim 18, comprising an incontinence pad.

* * * * *

UNITED STATES PATENT AND TRADEMARK OFFICE
CERTIFICATE OF CORRECTION

PATENT NO. : 6,965,058 B1
DATED : November 15, 2005
INVENTOR(S) : Maria Raidel et al.

It is certified that error appears in the above-identified patent and that said Letters Patent is hereby corrected as shown below:

<u>Column 21,</u>
Line 2, delete "fibrous" and insert -- fibrous material --.

Signed and Sealed this

Seventh Day of March, 2006

JON W. DUDAS
*Director of the United States Patent and Trademark Office*